US009375338B2

(12) United States Patent
Baker et al.

(10) Patent No.: US 9,375,338 B2
(45) Date of Patent: Jun. 28, 2016

(54) INTRALUMINAL DEVICE AND METHOD WITH ENHANCED ANTI-MIGRATION

(75) Inventors: Randal S. Baker, Ada, MI (US); Frederick J. Walburn, Grand Rapids, MI (US); James A. Foote, Ada, MI (US)

(73) Assignee: BFKW, LLC, Grand Rapids, MI (US)

( * ) Notice: Subject to any disclaimer, the term of this patent is extended or adjusted under 35 U.S.C. 154(b) by 397 days.

(21) Appl. No.: 14/118,731

(22) PCT Filed: May 18, 2012

(86) PCT No.: PCT/US2012/038480
§ 371 (c)(1),
(2), (4) Date: Nov. 19, 2013

(87) PCT Pub. No.: WO2012/162114
PCT Pub. Date: Nov. 29, 2012

(65) Prior Publication Data
US 2014/0121585 A1    May 1, 2014

Related U.S. Application Data

(60) Provisional application No. 61/488,194, filed on May 20, 2011, provisional application No. 61/607,338, filed on Mar. 6, 2012.

(51) Int. Cl.
*A61M 5/00* (2006.01)
*A61F 5/00* (2006.01)
*A61F 2/04* (2013.01)

(52) U.S. Cl.
CPC ............... *A61F 5/0079* (2013.01); *A61F 2/04* (2013.01); *A61F 2002/045* (2013.01)

(58) Field of Classification Search
CPC ... A61F 5/0076; A61F 5/0083; A61F 5/0036; A61F 5/0089; A61F 2/04; A61F 2002/044; A61F 2002/045; A61M 27/002; A61B 17/1114

USPC ................ 604/8–9; 623/23.65–23.7
See application file for complete search history.

(56) References Cited

U.S. PATENT DOCUMENTS

| 4,403,604 A | 9/1983 | Wilkinson et al. |
| 4,607,618 A | 8/1986 | Angelchik |

(Continued)

FOREIGN PATENT DOCUMENTS

| JP | 2660101 B2 | 6/1997 |
| JP | 2011509758 A | 3/2011 |

(Continued)

OTHER PUBLICATIONS

International Preliminary Report on Patentability from corresponding Patent Cooperation Treaty Patent Application No. PCT/US2012/038480 issued Nov. 20, 2013.

(Continued)

*Primary Examiner* — Philip R Wiest
(74) *Attorney, Agent, or Firm* — Gardner, Linn, Burkhart & Flory, LLP

(57) ABSTRACT

An intraluminal device and method includes positioning the intraluminal device, such as a bariatric device, in a lumen that is subject to peristaltic waves, such as the GI tract. The intraluminal device includes a surface defined by a wall having opposite end portions. The surface is configured to generally conform to the shape and size of a portion of the lumen. The end portions are spaced apart along an axis in the direction of peristaltic movement along the lumen. The cover has at least one opening therein between the end portions in order to resist peristaltic waves causing distal migration of the device.

33 Claims, 17 Drawing Sheets

(56) References Cited

U.S. PATENT DOCUMENTS

| | | |
|---|---|---|
| 5,234,454 A | 8/1993 | Bangs |
| 5,306,300 A | 4/1994 | Berry |
| 5,507,755 A | 4/1996 | Gresl et al. |
| 5,662,713 A | 9/1997 | Andersen et al. |
| 5,741,279 A | 4/1998 | Gordon et al. |
| 5,820,584 A | 10/1998 | Crabb |
| 6,146,416 A * | 11/2000 | Andersen .................. A61F 2/90 623/1.15 |
| 6,355,070 B1 | 3/2002 | Andersen et al. |
| 6,432,040 B1 | 8/2002 | Meah |
| 6,544,291 B2 | 4/2003 | Taylor |
| 6,558,400 B2 | 5/2003 | Deem et al. |
| 6,572,627 B2 | 6/2003 | Gabbay |
| 6,656,194 B1 | 12/2003 | Gannoe et al. |
| 6,675,809 B2 | 1/2004 | Stack et al. |
| 6,736,828 B1 | 5/2004 | Adams et al. |
| 6,740,121 B2 | 5/2004 | Geitz |
| 6,746,460 B2 | 6/2004 | Gannoe et al. |
| 6,755,869 B2 | 6/2004 | Geitz |
| 6,773,440 B2 | 8/2004 | Gannoe et al. |
| 6,802,868 B2 | 10/2004 | Silverman et al. |
| 6,845,776 B2 | 1/2005 | Stack et al. |
| 6,960,233 B1 | 11/2005 | Berg et al. |
| 6,981,978 B2 | 1/2006 | Gannoe |
| 6,994,095 B2 | 2/2006 | Burnett |
| 6,994,715 B2 | 2/2006 | Gannoe et al. |
| 7,025,791 B2 | 4/2006 | Levine et al. |
| 7,033,373 B2 | 4/2006 | de la Torre et al. |
| 7,033,384 B2 | 4/2006 | Gannoe et al. |
| 7,037,344 B2 | 5/2006 | Kagan et al. |
| 7,044,979 B2 | 5/2006 | Silverman et al. |
| 7,066,945 B2 | 6/2006 | Hashiba et al. |
| 7,083,629 B2 | 8/2006 | Weller et al. |
| 7,083,630 B2 | 8/2006 | DeVries et al. |
| 7,087,088 B2 | 8/2006 | Berg et al. |
| 7,097,650 B2 | 8/2006 | Weller et al. |
| 7,097,665 B2 | 8/2006 | Stack et al. |
| 7,146,984 B2 | 12/2006 | Stack et al. |
| 7,152,607 B2 | 12/2006 | Stack et al. |
| 7,220,284 B2 | 5/2007 | Kagan et al. |
| 7,232,461 B2 | 6/2007 | Ramer |
| 7,347,875 B2 | 3/2008 | Levine et al. |
| 7,431,725 B2 | 10/2008 | Stack et al. |
| 7,445,010 B2 | 11/2008 | Kugler et al. |
| 7,682,330 B2 | 3/2010 | Meade et al. |
| 7,708,752 B2 | 5/2010 | Durgin |
| 7,771,382 B2 | 8/2010 | Levine et al. |
| 7,815,589 B2 | 10/2010 | Meade et al. |
| 7,815,591 B2 | 10/2010 | Levine et al. |
| 7,846,174 B2 | 12/2010 | Baker et al. |
| 7,976,488 B2 | 7/2011 | Levine et al. |
| 7,981,163 B2 | 7/2011 | Meade et al. |
| 8,029,455 B2 | 10/2011 | Stack et al. |
| 8,043,355 B2 | 10/2011 | Shin et al. |
| 8,100,931 B2 | 1/2012 | Baker et al. |
| 8,137,301 B2 | 3/2012 | Levine et al. |
| 8,162,871 B2 | 4/2012 | Levine et al. |
| 8,282,598 B2 | 10/2012 | Belhe et al. |
| 8,372,087 B2 | 2/2013 | Baker et al. |
| 8,529,431 B2 | 9/2013 | Baker et al. |
| 8,894,670 B2 | 11/2014 | Baker et al. |
| 2001/0020189 A1 | 9/2001 | Taylor |
| 2002/0032487 A1 | 3/2002 | Dua et al. |
| 2002/0091395 A1 | 7/2002 | Gabbay et al. |
| 2004/0117031 A1 | 6/2004 | Stack et al. |
| 2004/0138761 A1 | 7/2004 | Stack et al. |
| 2004/0143342 A1 | 7/2004 | Stack et al. |
| 2004/0172141 A1 | 9/2004 | Stack et al. |
| 2004/0220682 A1 | 11/2004 | Levine et al. |
| 2005/0080395 A1 | 4/2005 | Levine et al. |
| 2005/0096728 A1 | 5/2005 | Ramer |
| 2005/0125020 A1 | 6/2005 | Meade et al. |
| 2005/0197715 A1 | 9/2005 | Kugler et al. |
| 2005/0228504 A1 | 10/2005 | Demarais |
| 2005/0245788 A1 | 11/2005 | Gerber |
| 2005/0245957 A1 | 11/2005 | Starkebaum et al. |
| 2005/0247320 A1 | 11/2005 | Stack et al. |
| 2005/0251176 A1 | 11/2005 | Swanstrom et al. |
| 2005/0283235 A1 | 12/2005 | Kugler et al. |
| 2006/0020277 A1 | 1/2006 | Gostout et al. |
| 2006/0036293 A1 | 2/2006 | Whitehurst et al. |
| 2006/0064120 A1 | 3/2006 | Levine et al. |
| 2006/0074473 A1 | 4/2006 | Gertner |
| 2006/0089571 A1 | 4/2006 | Gertner |
| 2006/0149307 A1 | 7/2006 | Durgin |
| 2006/0155375 A1 | 7/2006 | Kagan et al. |
| 2006/0161139 A1 | 7/2006 | Levine et al. |
| 2006/0190019 A1 | 8/2006 | Gannoe et al. |
| 2006/0253131 A1 | 11/2006 | Wolniewicz, III |
| 2006/0264699 A1 | 11/2006 | Gertner |
| 2006/0265082 A1 | 11/2006 | Meade et al. |
| 2007/0005147 A1 | 1/2007 | Levine et al. |
| 2007/0010866 A1 | 1/2007 | Dann et al. |
| 2007/0166396 A1 | 7/2007 | Badylak et al. |
| 2007/0179590 A1 | 8/2007 | Lu et al. |
| 2007/0208429 A1 | 9/2007 | Leahy |
| 2007/0276432 A1 | 11/2007 | Stack et al. |
| 2007/0293716 A1 | 12/2007 | Baker et al. |
| 2008/0015523 A1 | 1/2008 | Baker |
| 2008/0065136 A1 | 3/2008 | Young |
| 2008/0215076 A1 * | 9/2008 | Baker ................ A61B 17/1114 606/154 |
| 2008/0312678 A1 | 12/2008 | Pasricha |
| 2009/0177215 A1 | 7/2009 | Stack et al. |
| 2009/0240340 A1 | 9/2009 | Levine et al. |
| 2009/0248171 A1 | 10/2009 | Levine et al. |
| 2010/0030017 A1 * | 2/2010 | Baker .............. A61B 17/00234 600/37 |
| 2010/0063518 A1 | 3/2010 | Baker et al. |
| 2010/0114130 A1 | 5/2010 | Meade et al. |
| 2010/0198237 A1 | 8/2010 | Baker et al. |
| 2011/0009690 A1 | 1/2011 | Belhe et al. |
| 2011/0092879 A1 | 4/2011 | Baker et al. |
| 2012/0089168 A1 | 4/2012 | Baker et al. |
| 2012/0289991 A1 | 11/2012 | Baker |
| 2013/0123811 A1 | 5/2013 | Baker et al. |
| 2013/0296913 A1 | 11/2013 | Foote et al. |

FOREIGN PATENT DOCUMENTS

| | | |
|---|---|---|
| RU | 2045233 C1 | 10/1995 |
| RU | 94026119 A1 | 8/1996 |
| WO | 9322986 A1 | 11/1993 |
| WO | 9412136 A1 | 6/1994 |
| WO | 0135834 A1 | 5/2001 |
| WO | 0185034 A1 | 11/2001 |
| WO | 02060328 A1 | 8/2002 |
| WO | 02094105 A2 | 11/2002 |
| WO | 2004064685 A1 | 8/2004 |
| WO | 2005037152 A1 | 4/2005 |
| WO | 2006044640 A1 | 4/2006 |
| WO | 2009091899 A2 | 7/2009 |
| WO | 2011116025 A1 | 9/2011 |

OTHER PUBLICATIONS

Commonly assigned copending U.S. Appl. No. 14/572,230, filed Dec. 16, 2014, entitled Endoscopic Fixation of a Medical Device Using Mucosal Capture.

International Search Report and Written Opinion of the International Searching Authority from corresponding Patent Cooperation Treaty (PCT) Patent Application No. PCT/US12/38480, mailed Jul. 30, 2012.

Andrew S. Lowe, M.D. and Maria B. Sheridan, M.D., "Esphogeal Stenting", Seminars in Interventional Radiology, vol. 21, No. 3, 2004, pp. 157-166.

Andrew F.R. Dixon, Johgn B. Dixon, and Paul E. O'Brien, "Laparoscopic Adjustable Gastric Banding Induces Prolonged Satiety: A Randomized Blind Crossover Study", The Journal of Clinical Endocrinology & Metabolism , pp. 813-819, 2005.

Summary of Official Action dated Oct. 29, 2009, from the Israel Patent Office in a patent application corresponding to the present application.

(56) References Cited

OTHER PUBLICATIONS

Commonly assigned co-pending U.S. Appl. No. 13/965,617, filed Aug. 13, 2013, entitled Bariatric Device and Method.
Commonly assigned copending U.S. Appl. No. 14/920,403, filed Oct. 22, 2015, entitled Bariatric Device and Method.
Commonly assigned copending U.S. Appl. No. 14/518,414, filed Oct. 20, 2014, entitled Mucosal Capture Fixation of Medical Device.
Schembre, Drew, "Advances in Esophageal Stenting: the Evolution of Fully Covered Stents for Malignant and Benign Disease," Adv. Ther., Springer Healthcare, Apr. 1, 2010, pp. 1-13.
"Obesity: Super-Sized Medical Device Market", Start-Up, Mar. 2003, Technology Strategies (Long Article), pp. 1-10 and a cover page.
Andrew S. Lowe, M.D. and Mara B. Sheridan, M.D., "Esphogeal Stenting", Seminars in Interventional Radiology, vol. 21; No. 3, 2004, pp. 157-166.
"Polyflex® Espohageal Stent", Silicone Covered Stent, Boston Scientific, three pages. (2003).
Andrew F.R. Dixon, Johgn B. Dixon, and Paul E. O'Brien, "Laparoscopic Adjustable Gastric Banding induces Prolonged Satiety: A Randomized Blind Crossover Study", The Journal of Clinical Endocrinology & Metabolism, pp. 813-819, 2005.
Roman, S. et al., "Intragastric balloon for 'non-morbid' obesity: a retrospective evaluation of tolerance and efficacy," Obes. Surg., 2004, 14(4), 539-44, abstract, [on-line], [found Apr. 17, 2009, from Pubmed database].
Busetto, L. et al., "Preoperative weight loss by intragastric balloon in super-obese patients treated with laparoscopic gastric banding: a case-control study," Obes Surg., 2004, 14(5), 671-6, abstract, [on-line], [found Apr. 17, 2009, from Pubmed database].
Summary of Official Action dated Oct. 29, 2009, from the Israel Patent Office in a patent application corresponding to the present application.
Lowe, Andrew S., M.D. and Sheridan, Maria B., M.D., "Esophageal Stenting," annotated by Israel Patent Office (2004).
Abstract and claims of U.S. Pat. No. 6,960,233 annotated by the Israel Patent Office (Nov. 1, 2005).
Commonly assigned co-pending U.S. Appl. No. 13/965,617, filed on Aug. 13, 2013, entitled Bariatric Device and Method.

\* cited by examiner

INTRALUMINAL DEVICE AND METHOD WITH ENHANCED ANTI-MIGRATION

CROSS REFERENCE TO RELATED APPLICATIONS

This application claims the priority benefits of International Patent Application No. PCT/US2012/038480 filed on May 18, 2012, which claims priority from U.S. patent application Ser. No. 61/488,194, filed on May 20, 2011, and U.S. patent application Ser. No. 61/607,338, filed on Mar. 6, 2012, the disclosures of which are hereby incorporated herein by reference in their entirety.

BACKGROUND OF THE INVENTION

The present invention is directed to an intraluminal device and method and, in particular, to such a device and method that are useful in a lumen that is subject to peristaltic waves to resist distal migration of the device from the action of the peristaltic waves. While the invention is illustrated as a bariatric device and method having an esophageal member that is adapted to be positioned in the esophagus, it may be useful with other devices and methods in the esophagus as well as devices and methods useful in other lumens that are subject to peristaltic waves.

SUMMARY OF THE INVENTION

An intraluminal device and method, according to an aspect of the invention, includes positioning the intraluminal device in a lumen that is subject to peristaltic waves. The intraluminal device includes a surface defined by a wall having opposite end portions. The surface is configured to generally conform to the shape and size of a portion of the lumen. The end portions are spaced apart along an axis in the direction of peristaltic movement along the lumen. The wall has at least one opening therein between the end portions in order to resist peristaltic waves causing distal migration of the device.

The at least one opening may be at least two openings that are spaced apart a distance that is at least on the order of magnitude of a wavelength of the peristaltic wave in the lumen. The wall may be generally cylindrical with respect to the axis and the opening(s) may include a pattern that is distributed radially around a circumference of the wall. The opening(s) may include at least two openings, with the pattern being at least two patterns that are distributed radially around a circumference of the wall. The patterns may be arranged generally perpendicular to the axis. The patterns may be spaced apart a distance that is on the order of magnitude of a wavelength of a peristaltic wave of the lumen and may be spaced apart a distance that is at least approximately the wavelength of the peristaltic wave of the lumen. Each pattern may be an open band extending substantially around the wall generally perpendicular to the axis. Alternatively, each said pattern may be a plurality of discrete openings extending substantially around the wall.

The wall may be defined by a support structure and a cover over the support structure with the opening(s) defined in the cover. The support structure may be defined by a plurality of crossing wire portions thereby defining a plurality of rectilinear polygons and wherein the opening(s) is the size of a plurality of adjacent ones of said polygons. The opening(s) may be the size of four of adjacent ones of the polygons arranged in a rectilinear polygon.

The opening(s) may be configured to regulate mucosal ingrowth on the support structure. The opening(s) may be configured to regulate mucosal ingrowth by having a dimension along the axis that is less than an amount that would promote mucosal ingrowth. The opening(s) may be configured to regulate mucosal ingrowth by the cover extending on a side of the support structure at the opening(s) that is opposite a side that is adapted to contact the mucosa.

The support structure may be a mesh. The mesh may be an outwardly expanding mesh. The mesh may have a non-uniform cell structure. The cell structure may be less dense proximally than distally thereby defining a transitional zone. The cover may extend proximally beyond the mesh thereby defining the transitional zone at least in part. The cover is thicker at one or both of the end portions.

The surface may be configured to generally conform to the shape and size of a portion of i) the esophagus, ii) the intestine, iii) the fallopian tube, iv) the ureter, v) the urethra, vi) the vas deferens, or vii) the biliary duct.

A bariatric device and method of causing at least partial satiety, according to an aspect of the invention, includes an esophageal member having an esophageal surface defined by an esophageal wall having an esophageal surface that is configured to generally conform to the shape and size of a portion of the esophagus and a cardiac member. The cardiac member has a cardiac wall defining a cardiac surface that is configured to generally conform to the shape and size of a portion of the cardiac region of the stomach. A connector connects the esophageal member and the cardiac member. The esophageal member and/or the cardiac member is adapted to stimulate receptors in order to influence a neurohormonal mechanism in the recipient to cause at least partial satiety by augmenting fullness caused by food and simulating fullness in the absence of food. The esophageal wall has end portions spaced apart along an axis in the direction of peristaltic movement along the esophagus and at least one opening therein between said end portions in order to resist peristaltic waves causing distal migration of the esophageal member.

The at least one opening may be at least two openings that are spaced apart a distance that is at least on the order of magnitude of a wavelength of the peristaltic wave of the esophagus. The esophageal wall may be generally cylindrical with respect to the axis and the opening(s) may include a pattern that is distributed radially around a circumference of the wall. The opening(s) may include at least two openings, with the pattern being at least two patterns that are distributed radially around a circumference of the wall. The patterns may be arranged generally perpendicular to the axis. The patterns may be spaced apart a distance that is on the order of magnitude of a wavelength of a peristaltic wave of the lumen and may be spaced apart a distance that is at least approximately the wavelength of the peristaltic wave of the lumen. Each pattern may be an open band extending substantially around the esophageal wall generally perpendicular to the axis. Alternatively, each said pattern may be a plurality of discrete openings extending substantially around the esophageal wall.

The esophageal wall may be defined by a support structure and a cover over the support structure with the opening(s) defined in the cover. The support structure may be defined by a plurality of crossing wire portions thereby defining a plurality of rectilinear polygons and wherein the opening(s) is the size of a plurality of adjacent ones of said polygons. The opening(s) may be the size of four of adjacent ones of the polygons arranged in a rectilinear polygon.

The opening(s) may be configured to regulate mucosal ingrowth on the support structure. The opening(s) may be configured to regulate mucosal ingrowth by having a dimension along the axis that is less than an amount that would promote mucosal ingrowth. The opening(s) may be configured to regulate mucosal ingrowth by the cover extending on a side of the support structure at the opening(s) that is opposite a side that is adapted to contact the mucosa.

The support structure may include a mesh. The mesh may be an outwardly expanding mesh. The mesh may have a non-uniform cell structure. The cell structure may be less dense proximally than distally thereby defining a transitional zone. The cover may extend proximally beyond the mesh thereby defining the transitional zone at least in part. The cover is thicker at one or both of the end portions.

A method of deploying an intraluminal device having a surface configured to generally conform to the shape and size of a portion of the lumen, according to an aspect of the invention, includes positioning an endoscopic device in the lumen and guiding a deployment device having the intraluminal device mounted thereto to the lumen with the endoscopic device. The intraluminal device is at least partially deployed from the deployment device in the lumen. The at least partially deployed intraluminal device is positioned with the deployment device while visualizing a position of the intraluminal device with the endoscopic device.

Deployment of the intraluminal device may be completed after it is positioned. The deployment device may include a deployment wall surrounding an opening. The deployment device can be guided by positioning the opening over the endoscopic device. The intraluminal device may be positioned around the deployment wall. The method may be performed without the use of fluoroscopy.

A method of deploying a bariatric device having an esophageal member with an esophageal surface is defined by an esophageal wall that is configured to generally conform to the shape and size of a portion of the esophagus and a cardiac member. The cardiac member has a cardiac wall defining a cardiac surface that is configured to generally conform to the shape and size of a portion of the cardiac region of the stomach. A connector connects the esophageal member and said cardiac member. The method, according to an aspect of the invention includes positioning an endoscopic device transorally in the stomach and guiding a deployment device having the bariatric device mounted thereto to the stomach with the endoscopic device. The bariatric device is at least partially deployed from the deployment device in the stomach. The bariatric device is positioned with the deployment device while visualizing a position of the bariatric device with the endoscopic device.

Deployment of the bariatric device may be completed after it is positioned. The deployment device may include a deployment wall surrounding an opening. The deployment device can be guided by positioning the opening over the endoscopic device. The bariatric device may be positioned around the deployment wall. The method may be performed without the use of fluoroscopy.

These and other objects, advantages and features of this invention will become apparent upon review of the following specification in conjunction with the drawings.

DESCRIPTION OF THE PREFERRED EMBODIMENT

Figure 1:
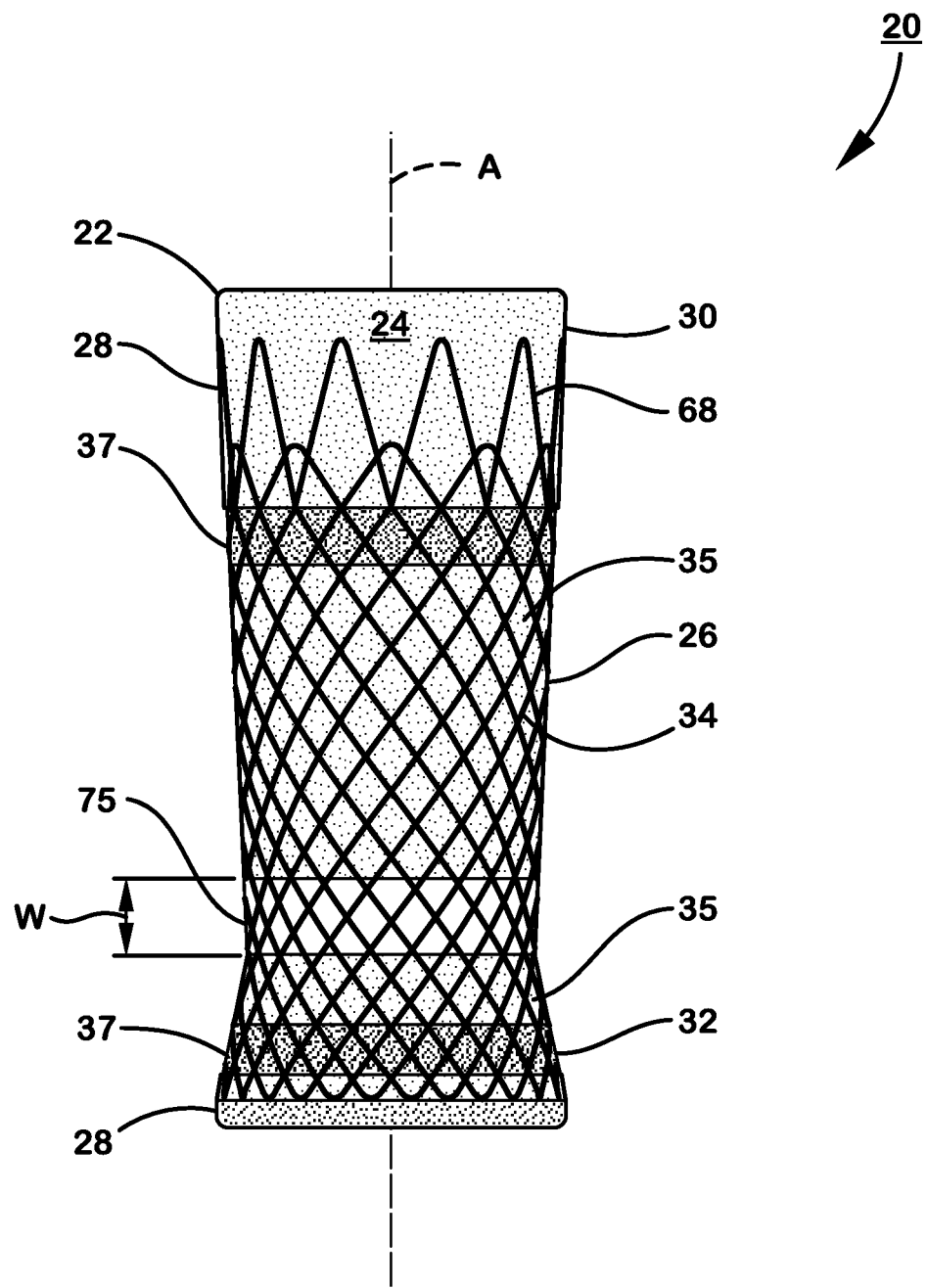
FIG. 1 is a side elevation of an intraluminal device according to an aspect of the invention.
Figure 2:
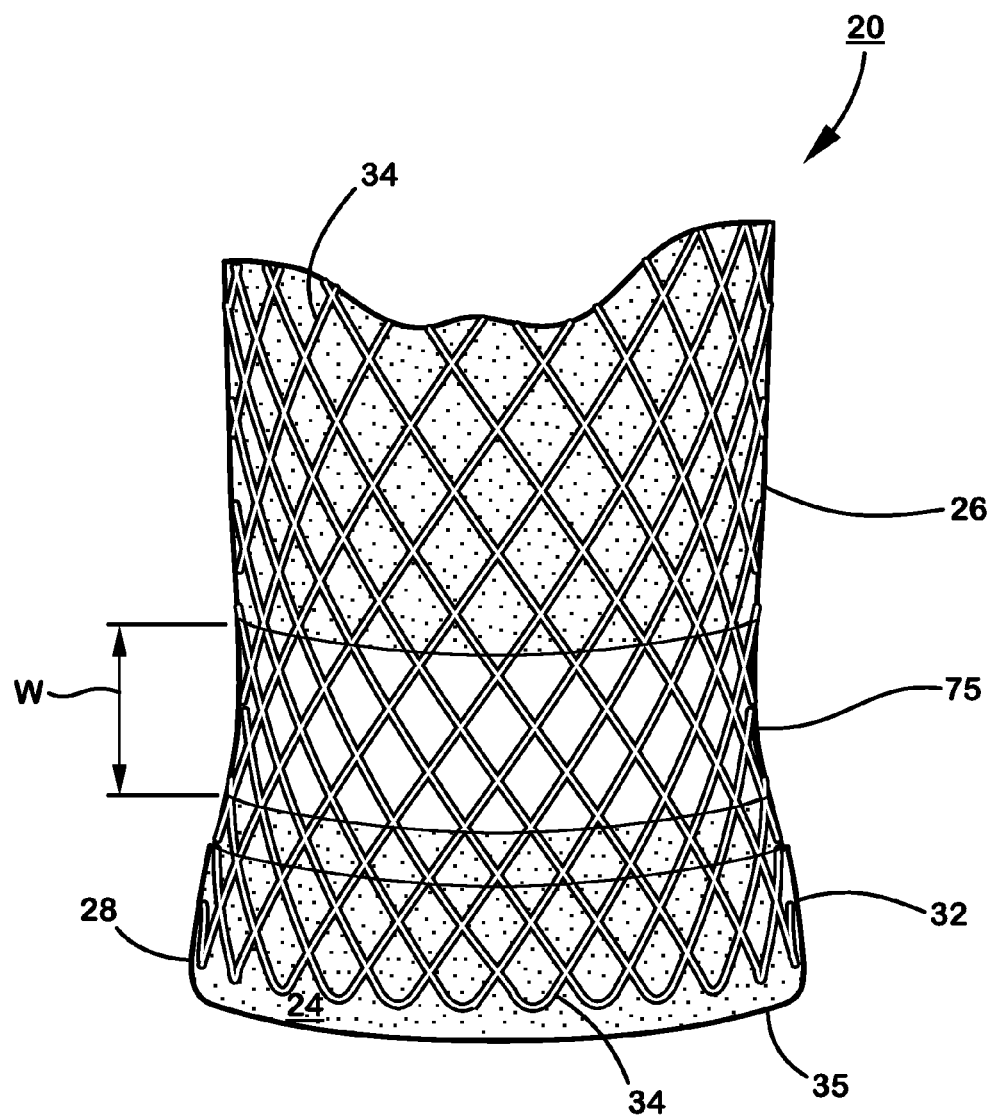
FIG. 2 is an enlarged perspective view of the area designated II in FIG. 1.

Referring now to the drawings and the illustrative embodiments depicted therein, an intraluminal device 20 includes a member, such as an esophageal member 22, having a surface 24 defined by a wall 26 having opposite end portions made up of a proximal end portion 30 and a distal end portion 32 (FIGS. 1 and 2). Surface 24 is configured to generally conform to the shape and size of a portion of the lumen in which it is to be deployed. In particular, surface 24 is configured to generally conform to the shape and size of a portion of a lumen that experiences peristalsis. Examples of such lumen include the esophagus, the colon, other portions of the intestines, ureter, urethra, biliary duct, fallopian tube, vas deferens, and the like.

End portions 30, 32 are spaced apart along an axis A in the direction of peristaltic movement along the lumen in which device 20 is deployed. Wall 26 is defined by a support structure, such as a wire mesh 34, made from Nitinol wire, or the like, and a cover 35 over support structure 34. In the illustrated embodiment, cover 35 is a form of silicone or other flexible biologically inert substance that is applied, for example, to about 0.4 millimeter thickness. Cover 34 may have one or more overlapped portions at proximal end portion and/or distal end portion 32. The layers of cover 35 are generally not adhered to each other where overlapped except at adhesive areas 37. This allows proximal end portion 30 and/or distal end portion 32 to be more pliant which produces transition zones 28 between device 20 and the lumen in which the device is deployed. Such transition zones are believed to minimize spasm as disclosed in commonly assigned U.S. patent application Ser. No. 61/388,857, filed Oct. 1, 2010, the disclosure of which is hereby incorporated herein by reference in its entirety. Transition zone 28 at proximal end portion 30 may additionally include a pattern 68 to mesh 34 that is less dense, or more open, than the pattern of the rest of mesh 34.

Intraluminal device 20 includes at least one opening 75 in cover 35. Opening 75 is between end portions 30, 32 and is provided in order to resist peristaltic waves causing distal migration of the device 20. Opening 75 provides an area where the mucosa of the lumen can grip device 20 between end portions 30, 32 by pooching into opening 75. This provides for capture of the mucosa of the lumen in which device 20 is positioned using the principles set forth in U.S. Patent Application Publication No. 2010/0198237 A1 entitled MUCOSAL CAPTURE FIXATION OF MEDICAL DEVICE, the disclosure of which is hereby incorporated herein by reference. The placement of opening 75 between end portions 30, 32 further assists in anchoring of the intraluminal device 20 within the lumen. While the principle of operation is not entirely known, it is believed that as the peristaltic wave passes down the lumen, it creates passing areas of increased inward pressure alternating with areas of decreasing pressure. Without opening 75, it may be possible to have an area of increasing pressure between end portions 30, 32 with areas of decreasing pressure nearby end portions 30, 32 thereby not having any portion of device 20 to resist distal migration, even were end portions 30, 32 to be left uncovered.

In the illustrated embodiment, opening 75 has a width W parallel to the axis A of device 20 that aligns with the direction of movement of the peristaltic wave. Opening 75 forms a pattern that is distributed radially around wall 26. This is accomplished in the illustrated embodiment by opening 75 being in the form of a band that extends around the wall. However, other shapes are possible as will be described in detail below.

Opening 75 is illustrated as a through-opening that promotes tissue ingrowth around the wires defining structure 34. Opening 75 may alternatively be configured to regulate the amount of mucosa ingrowth attachment to mesh 34, such as for ease of removal. This reduces the amount of effort required to remove device 20 from the lumen. One way to regulate mucosa ingrowth is to select width W of opening 75 to be less than a particular width. In the illustrated embodiment, width W is approximately 7.5 millimeters, but other dimensions are possible. Alternatively, or additionally, cover 35 may be essentially removed outwardly of mesh 34 at opening 75, but be present inwardly of mesh 75. This would allow the mucosa to pooch into opening 75, but be generally inhibited from growing around the strands of the mesh. However, even if mucosal ingrowth around the strands of the mesh were to occur which occurs when portions of the mucosa grow into each other in a manner that encompasses strands of mesh 34, which would aid in long term placement of device 20, techniques are known to remove the ingrowth, such as cautery. Also, a tool such as an endoscope, or the like, can be inserted between wall 26 and the esophagus in order to gently pry the mucosa away from opening 75.

In the illustrated embodiment, wall 26 is generally cylindrical with respect to axis A and opening 75 is in the shape of an open band that extends substantially entirely around wall 26 generally perpendicular to axis A. However, other shapes will be apparent to the skilled artisan. For example, discrete openings can be arranged in a pattern that extends substantially entirely around wall 26 generally perpendicular to axis A, as will be described in detail below.

Figure 3:
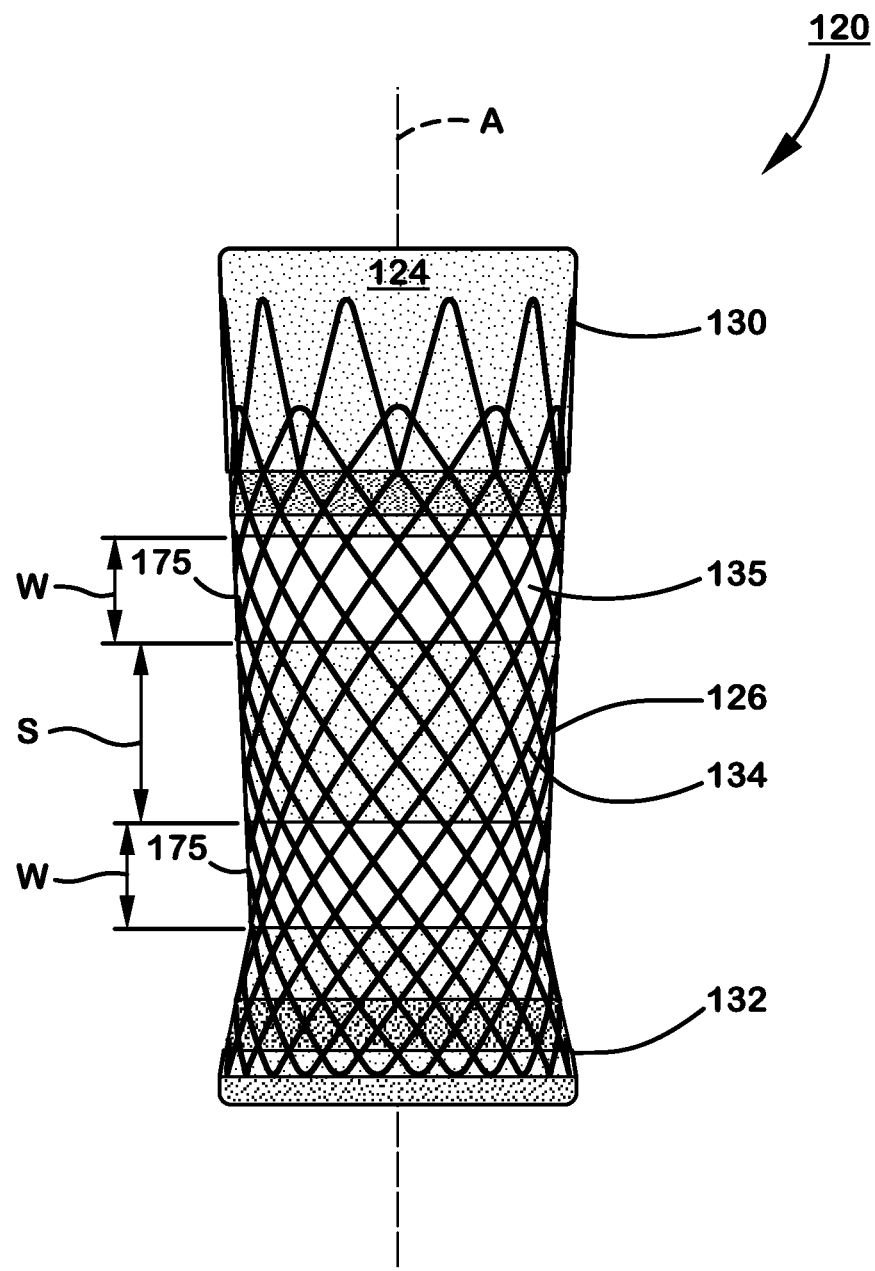
FIG. 3 is the same view as FIG. 1 of an alternative embodiment thereof.

In an alternative embodiment, an intraluminal device 120 includes a surface 124 defined by a wall 126 made up of a support structure, such as mesh 134 covered by a cover 135 (FIG. 3). Device 120 includes a plurality of openings that form patterns that extend around the circumference of wall 126 perpendicular to axis A that extends in the direction of movement of the peristaltic wave. These patterns are in the form of open bands 175 between a proximal end portion 130 and distal end portion 132. Bands 175 extend substantially around wall 126 generally perpendicular to axis A. Each opening 175 has a dimension W perpendicular to axis A that tends to regulate mucosa ingrowth, although other dimensions may be selected. Bands 175 are spaced apart a distance S that are on the order of magnitude of the wavelength of a peristaltic wave. In the illustrated embodiment, distance S is greater than or equal to the wavelength of a peristaltic wave. This ensures that, when an area of decreasing pressure of the lumen wall caused by the peristaltic wave passes over one band 175, an area of increasing pressure of the lumen wall will concurrently be passing over the other band 175 and vice versa. This ensures that there will typically be an area of increasing pressure acting on a band 175 to anchor the wall even with an area of decreasing pressure acting on the other band as the peristaltic wave passes in order to resist distal migration. In the illustrative embodiment, bands 175 are spaced apart a distance S that is greater than the wavelength of a peristaltic wave. By way of example, if the wavelength of the peristaltic wave is on the order of 1 to 2 centimeters, then distance S is approximately 2 to 3 centimeters or more. Although device 120 is illustrated with two bands 175, it should be understood that 3 or more bands may be used. Also, other patterns, such as discrete openings may be used.

In one application, intraluminal device 20 is a bariatric device and member 22 is an esophageal member that is configured to generally conform to the shape and size of the distal portion of the esophagus. As disclosed in commonly assigned U.S. Patent Application Publication No. 2007/0293716 A1, the disclosure of which is hereby incorporated herein by reference, such bariatric device stimulates receptors with surface 24 in order to influence a neurohormonal mechanism in the recipient sufficient to cause at least partial satiety by augmenting fullness caused by food and simulating fullness in the absence of food. However, intraluminal device 20 may, alternatively, be an esophageal stent configured to treat strictures, fistulas, and the like, in the esophagus. Intraluminal device 20 may, alternatively, be a colonic stent configured to treat stricture, fistulas, and the like, in the colon. Other applications will be apparent to the skilled artisan including stents configured to ureter, urethra, biliary duct, fallopian tube, vas deferens, and the like.

Figure 4:
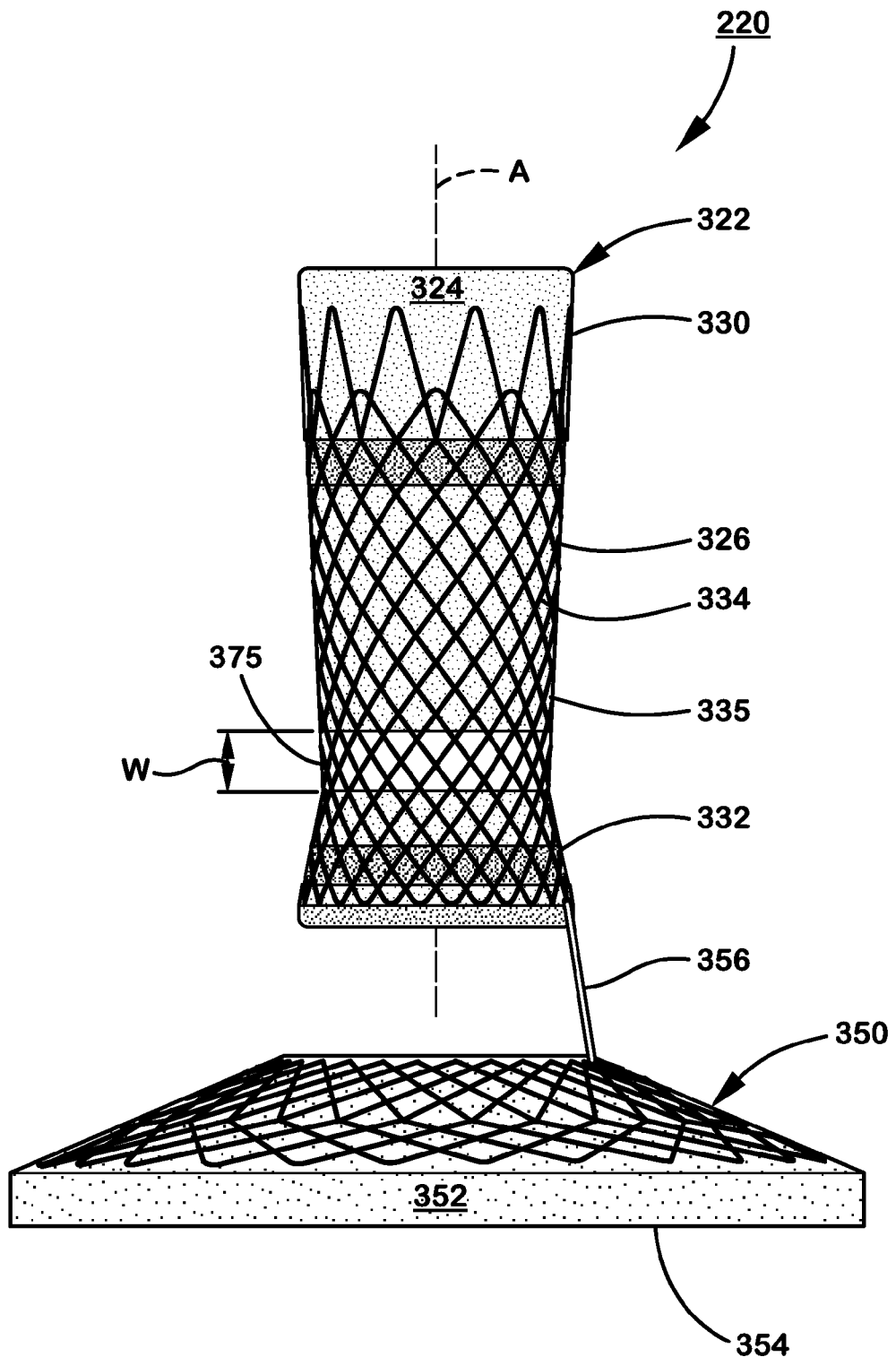
FIG. 4 is a side elevation of a bariatric device according to an aspect of the invention.
Figure 5:
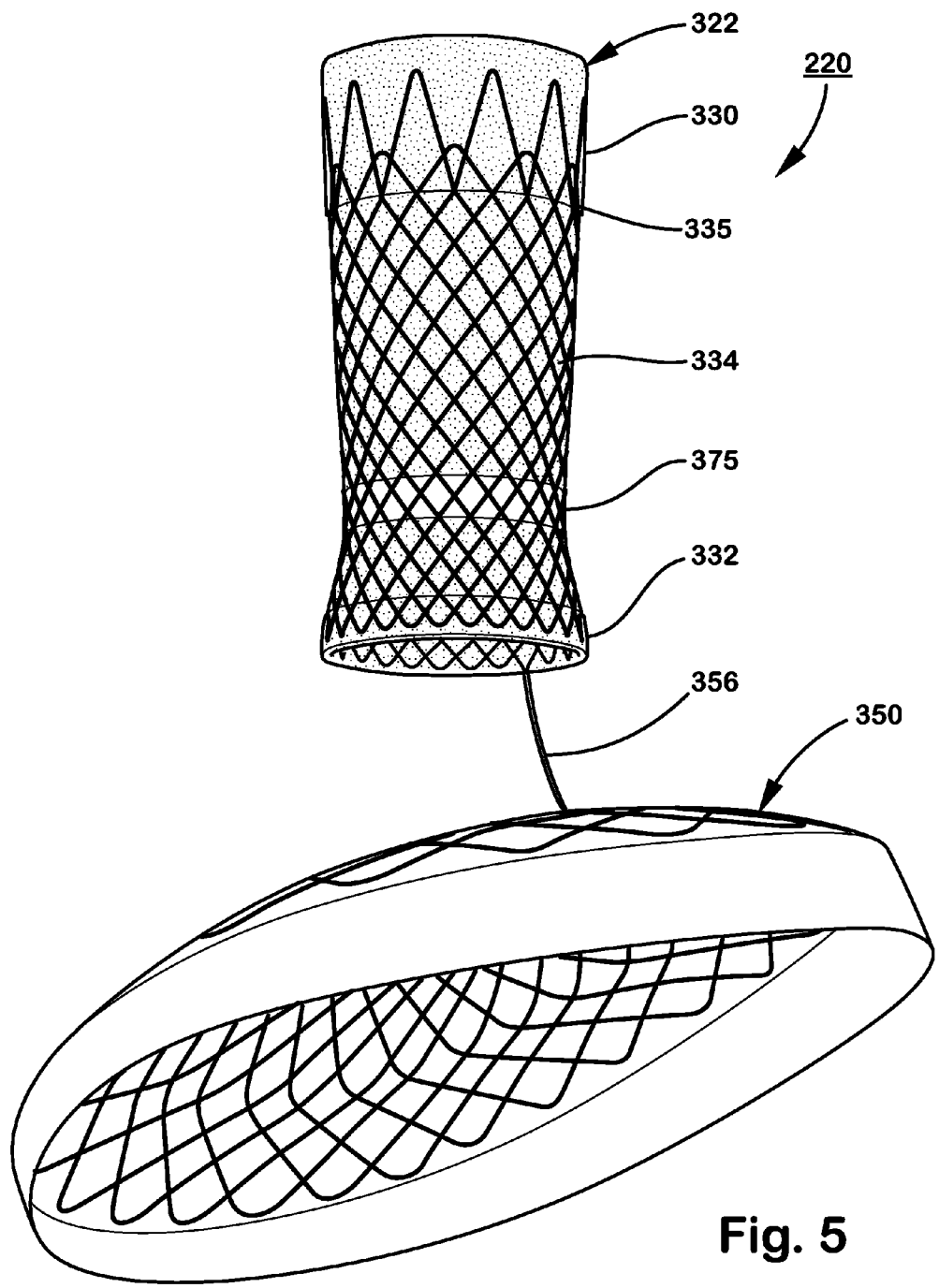
FIG. 5 is a perspective view of the bariatric device in FIG. 4.
Figure 6:
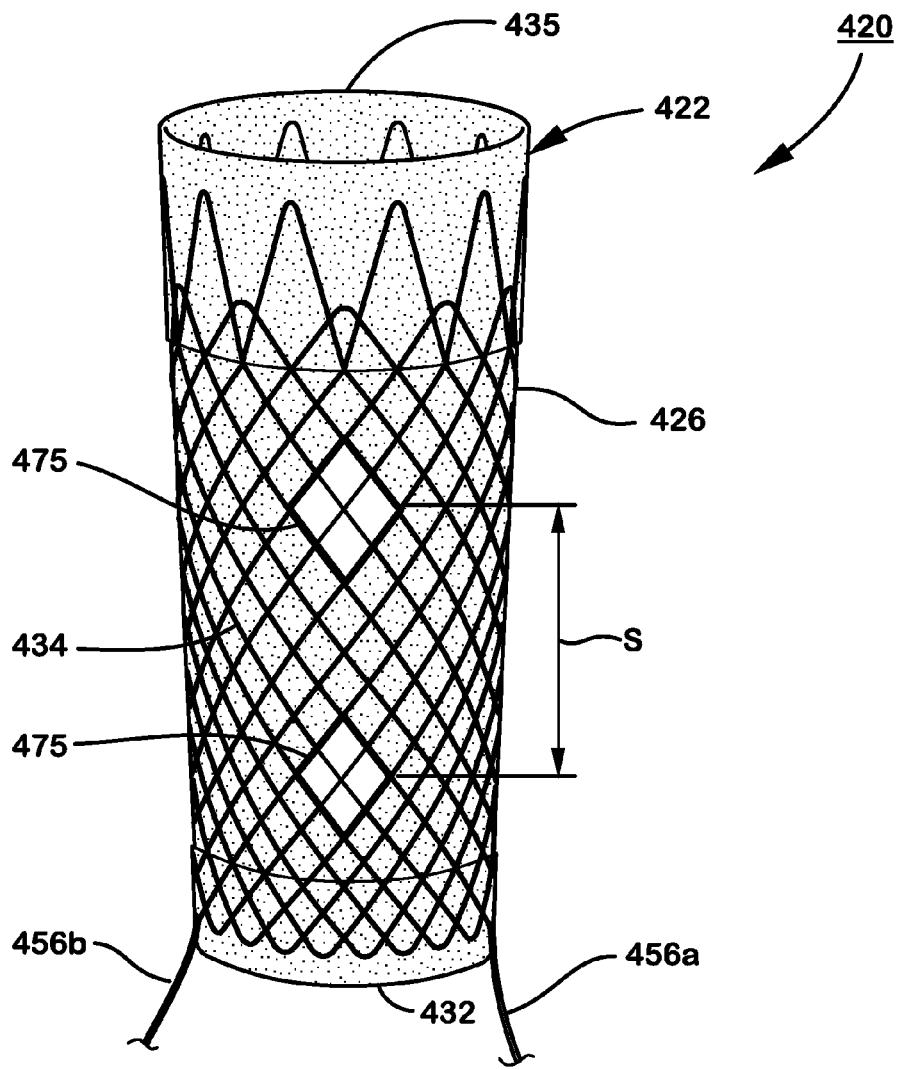
FIG. 6 is a perspective view of an esophageal member of an alternative embodiment of a bariatric device taken from the side thereof.

In another alternative embodiment, an intraluminal device 220 is in the form of a bariatric device having an esophageal member 322 having an esophageal surface 324 defined by an esophageal wall 336 (FIGS. 4 and 5). Esophageal surface 324 is configured to generally conform to the shape and size of a portion of the esophagus. Esophageal wall 336 has end portions 330, 332 that are spaced apart along an axis A in the direction of elongation of the esophagus, which is the direction of movement of the peristaltic waves. Wall 336 is defined by a support structure in the form of a mesh 334 and a cover 335 over mesh 334. Cover 335 has at least one 375 opening therein between end portions 330, 332 in order to resist peristaltic waves causing distal migration of esophageal member 322 in a similar fashion to bands 75 and 175 previously described.

Bariatric device 220 further includes a cardiac member 350 having a cardiac wall 354 defining a cardiac surface 352 that is configured to generally conform to the shape and size of a portion of the cardiac region of the stomach. Cardiac surface 352 and/or esophageal surface 324 are for the purpose of influencing a neurohormonal mechanism in the recipient sufficient to cause at least partial satiety by augmenting fullness caused by food and simulating fullness in the absence of food. Bariatric device 220 further includes a connector 356 connected with esophageal member 322 and cardiac member 350. Connector 356 passes through the pseudo-sphincter of the gastroesophageal junction in a manner that minimizes interference therewith. Tether devices may be installed in situ between esophageal member 322 and cardiac member 350 opposite connector 356 as disclosed in U.S. Patent Application Publication No. 2010/0030017 A1, the disclosure of which is hereby incorporated herein by reference. Connector 356 may have a radiopaque marker, such as gold thread extending along connector 356 in order to allow connector 356 to be properly positioned during deployment of bariatric device 220.

Figure 7:
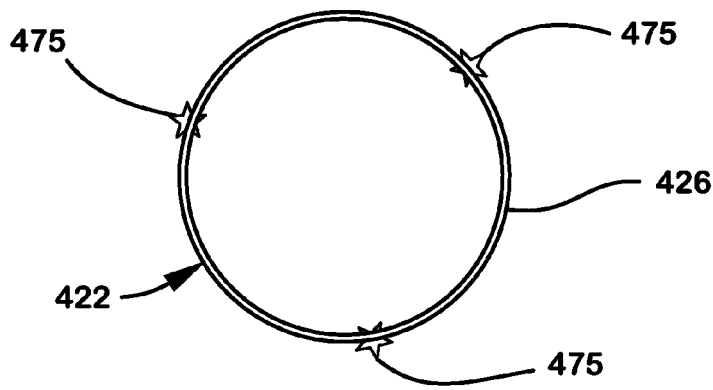
FIG. 7 is an end view of the esophageal member in FIG. 6.
Figure 8:
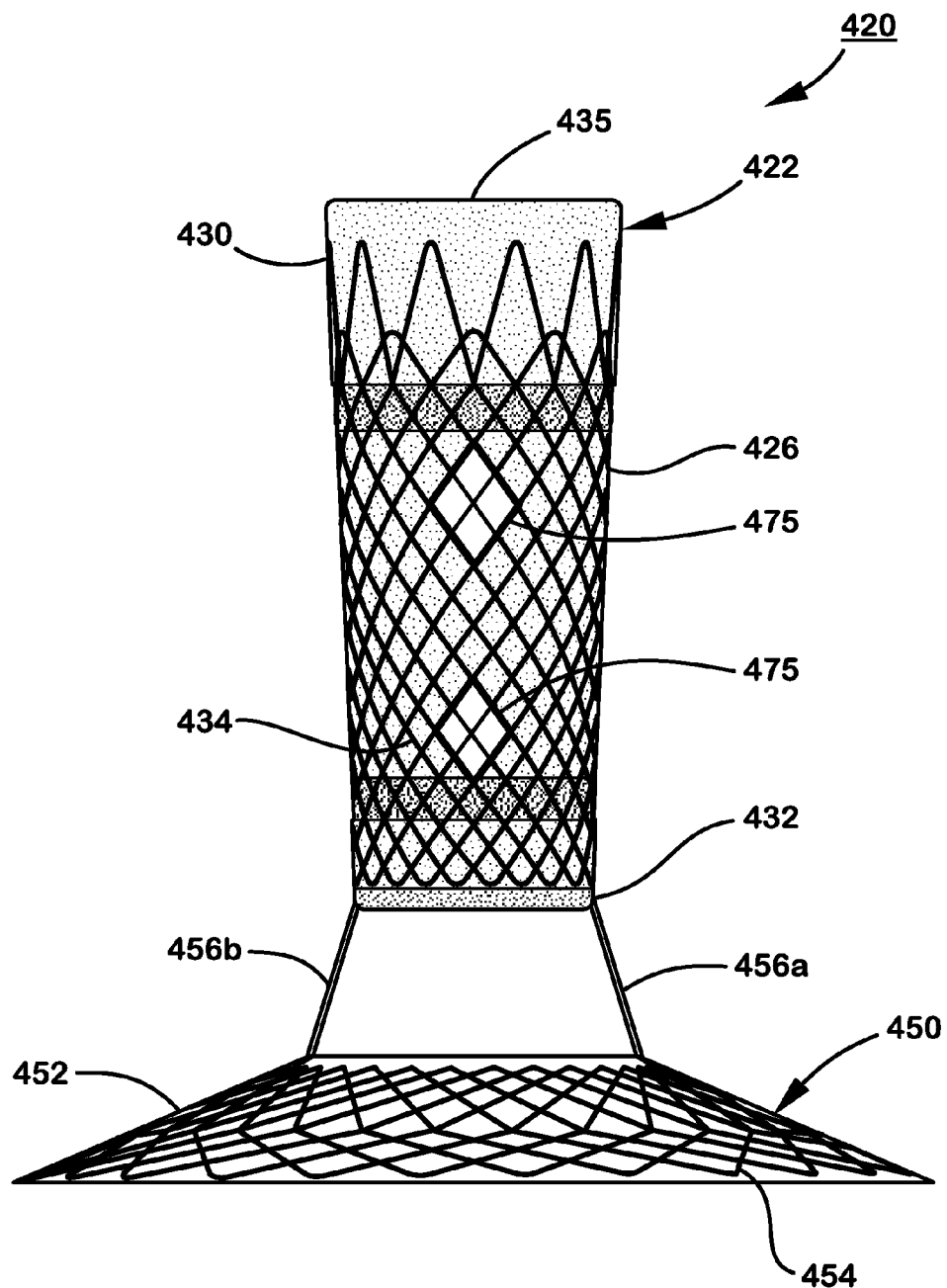
FIG. 8 is a side elevation of a bariatric device incorporating the esophageal member of FIG. 6.

In yet a further embodiment, a bariatric device 420 includes an esophageal member 422 having a cylindrically shaped wall 426 that expands to the general size and shape of the esophagus and a cardiac member 450 that expands to the general size and shape of the cardiac region of the stomach (FIGS. 6-9). Members 422 and 450 are connected with a connector 456 that passes through the GE junction in a manner that does not inhibit operation of the GE junction. Esophageal wall 426 is defined by a support, such as a mesh 434 that is covered by a cover such as a silicone cover 435 that defines a proximal end portion 430 and a distal end portion 432 with respect to propagation of the peristaltic waves. Esophageal wall 426 includes anchoring openings 475 between end portions 430, 432. Openings 475 are discrete openings that are arranged around the circumference of wall 426 in two patterns that are separated by distance S. As previously described, distance S is on the same magnitude as the peristaltic wavelength and is greater than or equal to the wavelength, yet openings 475 are inboard of end portions 430, 432. One pattern of openings 475 is illustrated in FIG. 7 in which three (3) openings 475 are spaced generally equidistant radially around the circumference of wall 426. While three (3) openings are illustrated in each pattern, a greater or lesser number could be used. Also, although openings 475 of each of the two patterns are generally aligned with each other in the direction of axis A, they could also be offset from each other.

In the illustrated embodiment, each opening 475 is made up of four (4) adjacent cells of mesh 434 in the form of a rectilinear polygon, such as a diamond shape. This allows pooching of the mucosa in openings 475 for immediate anchoring of esophageal member 422 and allows tissue ingrowth to occur around the wires interior to each opening 475 for longer term anchoring. In order to expedite tissue ingrowth, techniques may be used to irritate the mucosa to promote the growing together of the bulges pooching around the strands of the mesh. For example, a brush may be inserted endoscopically to the interior of esophageal member 422 to roughen the bulging mucosa. Also, various agents, such as sclerosants, may be applied to the bulging mucosa as described in U.S. Patent Application Publication 2010/0198237 A1. Also, each section of bulging mucosa may be suctioned individually, such as with an endoscope, to create a varix either by applying suction to each opening 475 or by applying suction to the entire esophageal member. A band, such as a rubber band, may be applied around the mucosa, such as from an end of an endoscope, to hold the bariatric device until tissue grows into each opening 475. At such time, the varix may fall off along with the rubber band and pass through the GI tract. Alternatively, each section of mucosa bulging into an opening 475 may be treated with injection of a bulking agent, such as various forms of injectable collagen, or the like. While the bulking agent will eventually be absorbed in the body, it will enlarge the bulging mucosa sufficiently to allow tissue in growth to occur. Other techniques will be apparent to the skilled artisan.

Connector 456 connects esophageal member 420 and cardiac member 450 in a manner that does not interfere with the operation of the GE junction. In the illustrated embodiment, connector 456 is made up of two or more tension members or struts 456a and 456b that are spaced apart roughly equal radial distances between the distal opening of esophageal member 422 and cardiac member 450. Struts 456a, 456b are shown oriented side-to-side in a frontal plane. If oriented in a frontal plane, one strut oriented at the greater curve will be longer in order to allow for the angled orientation of the cardiac member with respect to the esophageal member. Also, the strut 456a, 456b that is at the greater curve may be of a more flexible material than the other strut in order to conform to the curvature of the greater curve. Alternatively, the struts may be oriented anterior-posterior in a sagittal plane. If the struts are oriented on a sagittal plane, they may both be of generally the same length. The cardiac member will pivot into proper orientation against the cardiac portion of the stomach because it is free to pivot about the sagittal plane of struts 456a, 456b.

Figure 9:
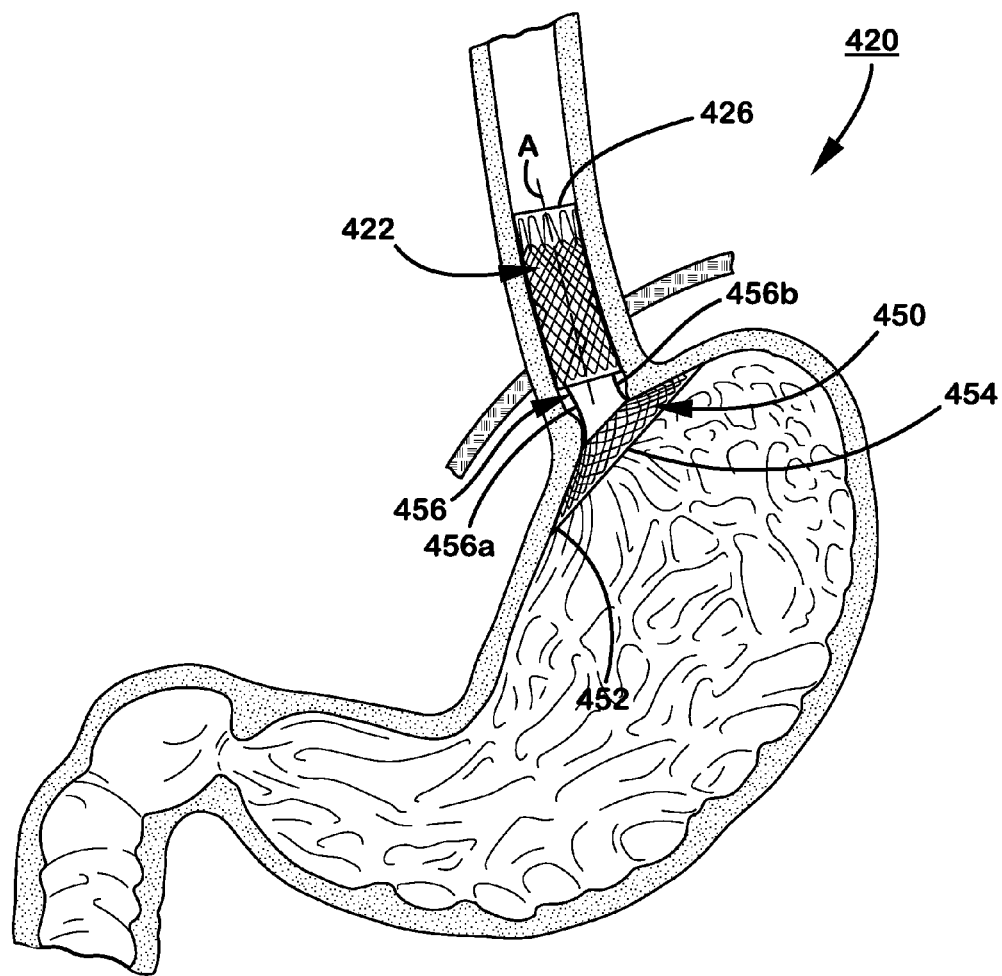
FIG. 9 is a view of the bariatric device of FIG. 8 deployed in a recipient.

In the illustrated embodiment, tension member 456a is approximately twice the length as tension member 456b, although dimensions may vary. This produces a tilt between cardiac member 450 and the axis A passing through esophageal member 422, as best seen in FIG. 9. This allows esophageal member 422 to pull cardiac member 450 via tension members 456a, 456b in a manner that applies a pressure against all portions of the cardia surrounding the GE junction notwithstanding the natural tilt of the greater and lesser curves of the stomach. In this manner, cardiac member 450 can apply pressure on the cardiac portion of the stomach solely by the anchoring of esophageal member 422 in the esophagus by openings 475. This eliminates the need for the use of additional anchoring mechanisms, such as the tethers disclosed in U.S. Patent Application Publication No. 2010/0030017 A1. However, other anchoring mechanisms can be used such as tissue ingrowth characteristics formed in cardiac surface 452 of cardiac member 450, or the like. In the illustrated embodiment, tension member 456a is 14 millimeters and tension member 456b is 7 millimeters. Tension members 456a, 456b may be made adjustable in length using the principles disclosed in U.S. Patent Application Publication No. 2010/0030017 A1 in order to titrate the amount of satiety achieved by the recipient as set forth in U.S. Pat. No. 8,100, 931, the disclosure of which is hereby incorporated herein by reference.

The recipient may be instructed to avoid solid foods for one or two weeks in order to allow tissue to grow around the mesh wires in openings 75, 175, and 475. If the device does migrate prior to the formation of tissue ingrowth, the recipient is not harmed because the device will reside in the stomach. The doctor can pull the device back into position. Alternatively, the device may be removed and redeployed with a suture looped around the esophageal portion. The suture may be attached such as to a molar of the recipient or a bracket of the type used by orthodontists temporarily fixed to a tooth. Such suture will be well tolerated by the recipient and can be clipped when no longer needed after tissue ingrowth has occurred.

Figure 10:
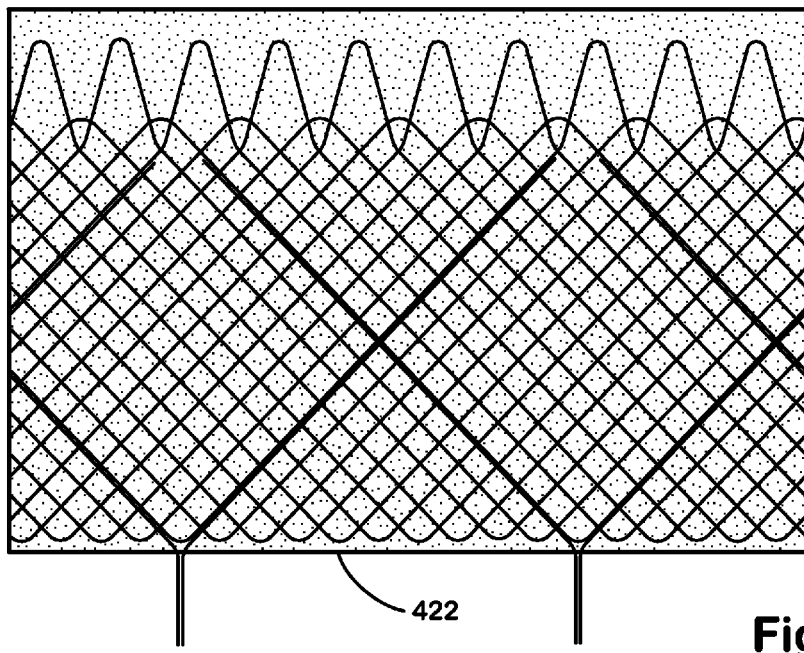
FIG. 10 is a side elevation of a flattened esophageal member showing a pattern of openings in a wall thereof.

FIG. 10 shows a bariatric device having an esophageal member 422 that has been flattened for better illustration and having no mucosal capture openings.

Figure 11:
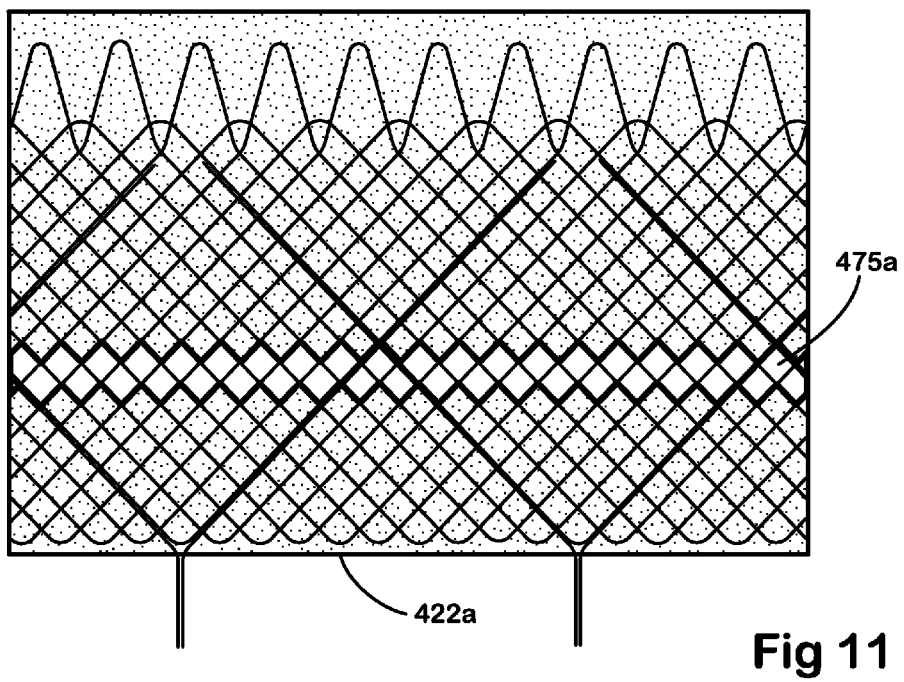
FIG. 11 is the same view as FIG. 10 of an alternative embodiment thereof.

FIG. 11 shows a bariatric device having an esophageal member 422a that has been flattened for better illustration and having mucosal capture openings 475a which are defined by a "Z" pattern defined by adjacent opened cells in the esophageal wall.

Figure 12:
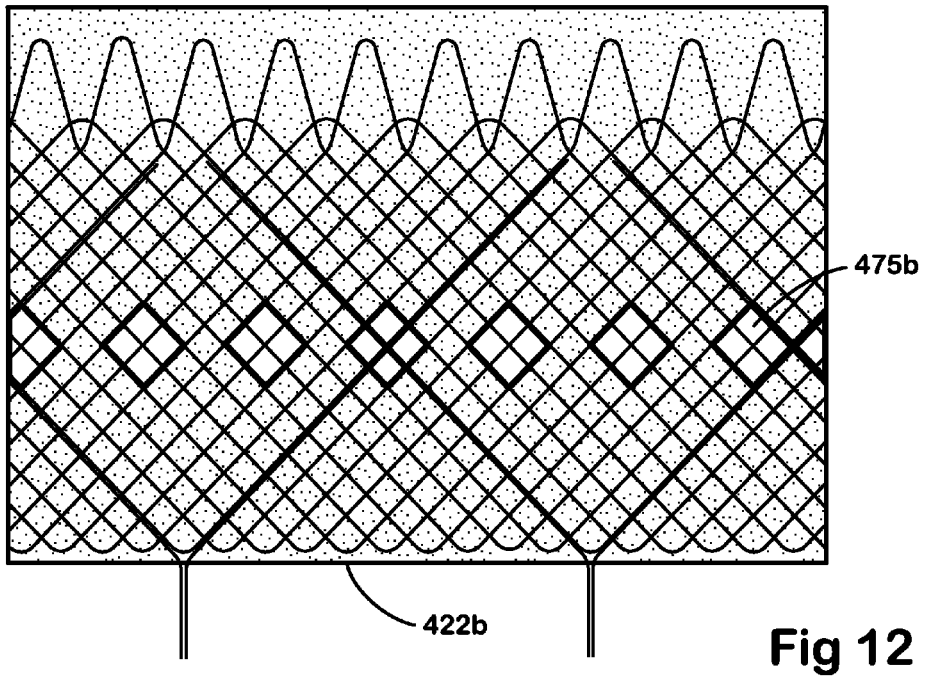
FIG. 12 is the same view as FIG. 10 of an alternative embodiment thereof.

FIG. 12 shows a bariatric device having a flattened esophageal member 422b having mucosal capture openings 475b that are arranged in a pattern of adjacent diamond shapes, each made up of four (4) open cells in the esophageal wall.

Figure 13:
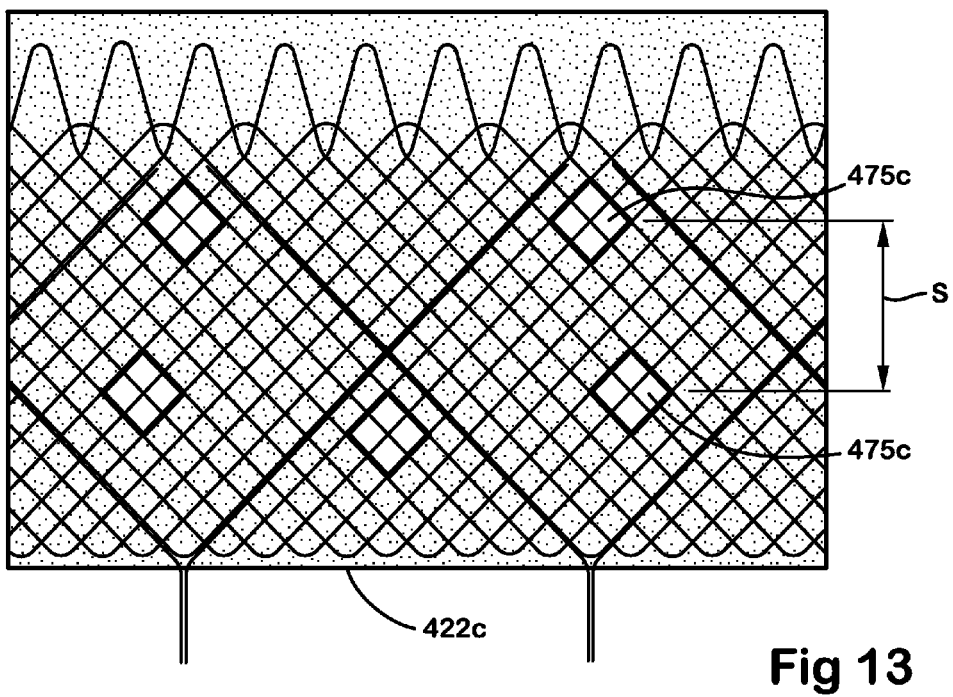
FIG. 13 is the same view as FIG. 10 of an alternative embodiment thereof.

FIG. 13 shows a bariatric device having a flattened esophageal member 422c having mucosal capture openings 475c that are diamond shapes, each made up of four (4) adjacent open cells of the mesh, with openings 475c being arranged in patterns that are spaced apart a distance "S" that is at least on the order of magnitude of the wavelength of the peristaltic wave in the esophagus.

Figure 14:
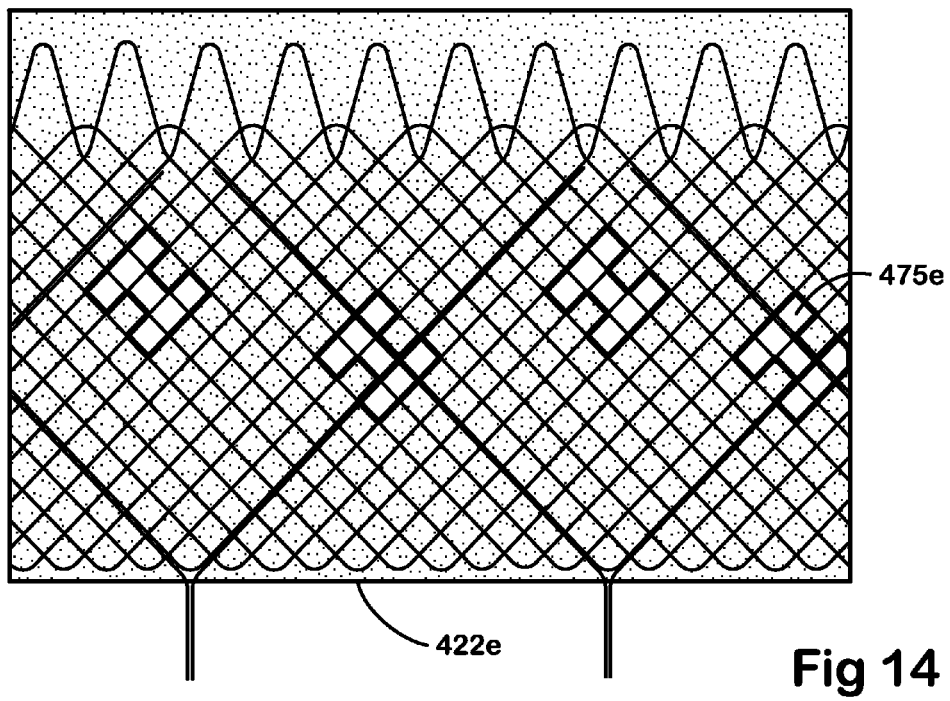
FIG. 14 is the same view as FIG. 10 of an alternative embodiment thereof.

FIG. 14 shows a bariatric device having a flattened esophageal member 422e having openings 475e, each in the shape of an "H" made up of three intersecting lines each encompassing three adjacent open cells of the mesh.

Figure 15:
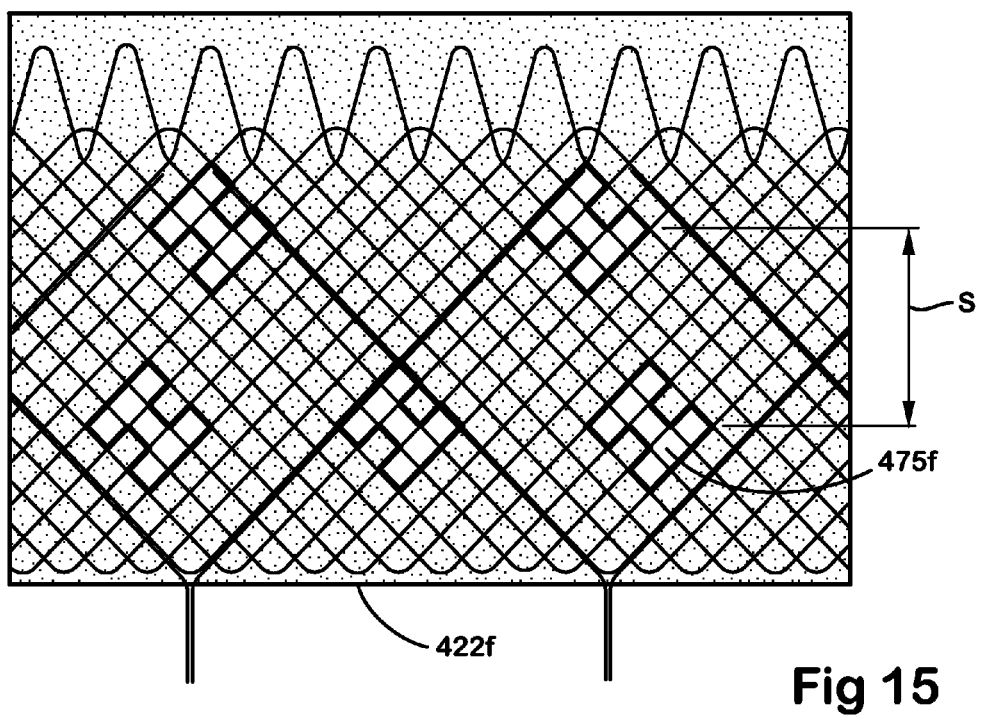
FIG. 15 is the same view as FIG. 10 of an alternative embodiment thereof.

FIG. 15 shows a bariatric device having a flattened esophageal member 422f, having a plurality of openings 475f each in a shape of an "H" similar to openings 475e, but arranged in patterns that are spaced apart a distance "S" that is at least on the order of magnitude of the wavelength of the peristaltic wave in the esophagus.

Figure 16:
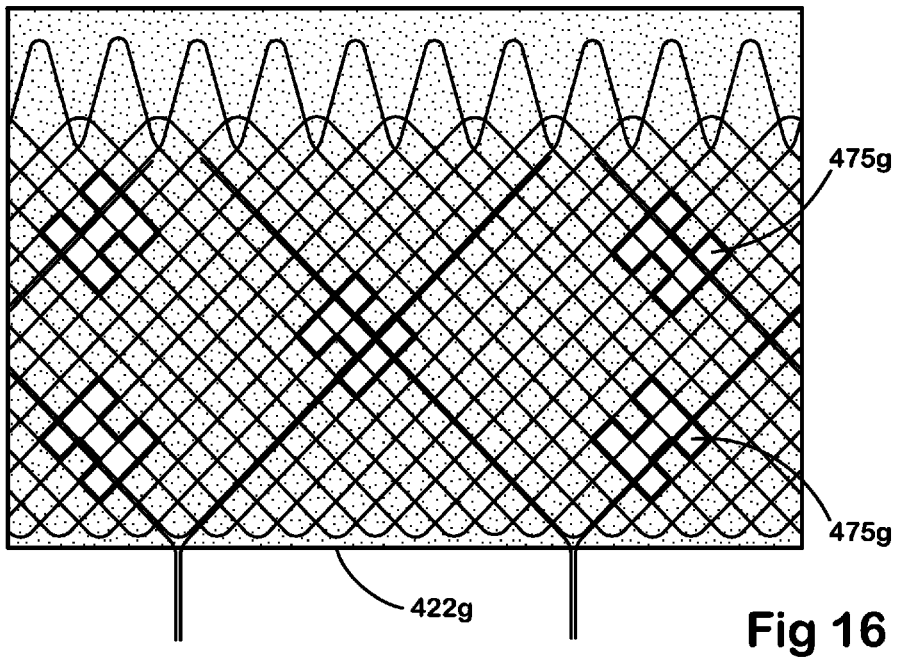
FIG. 16 is the same view as FIG. 10 of an alternative embodiment thereof.

FIG. 16 shows a bariatric device having a flattened esophageal member 422g having a plurality of openings 475g each in a shape of an "H" similar to openings 475e and 475f, but with the shapes having different orientations with each other.

Figure 17:
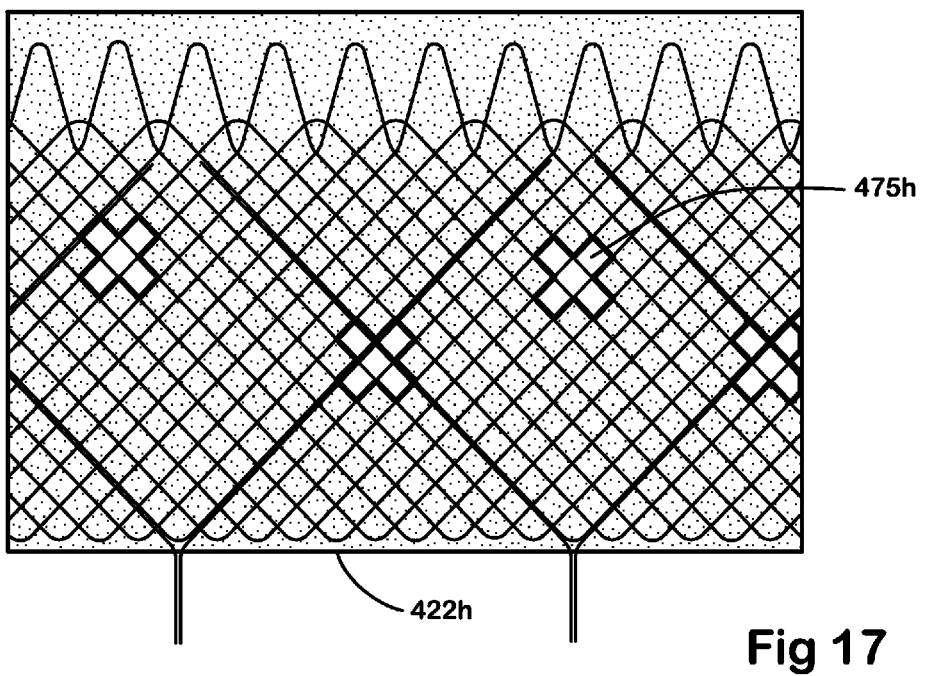
FIG. 17 is the same view as FIG. 10 of an alternative embodiment thereof.
Figure 18:
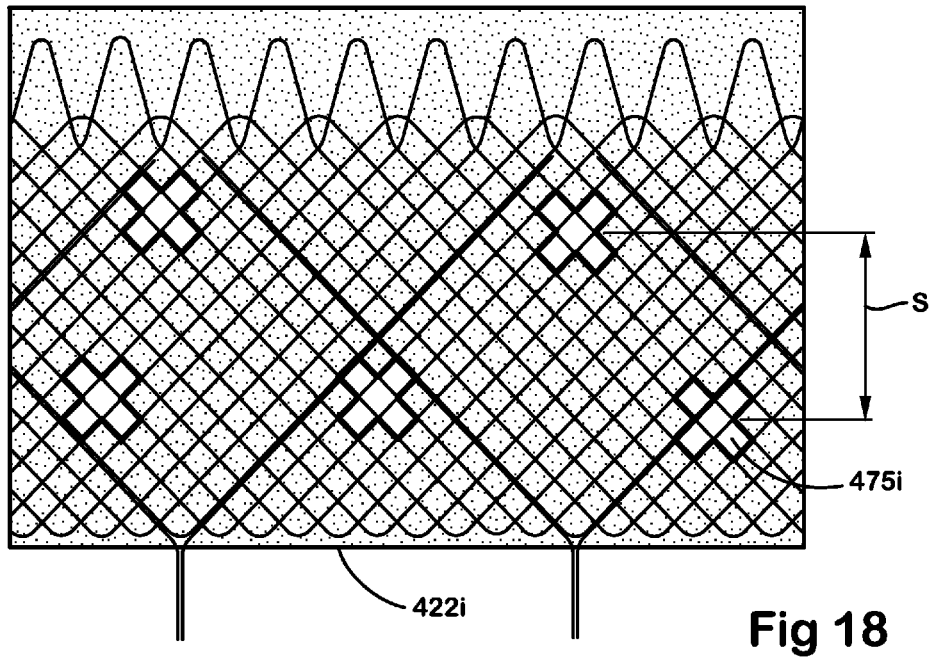
FIG. 18 is the same view as FIG. 10 of an alternative embodiment thereof.
Figure 19:
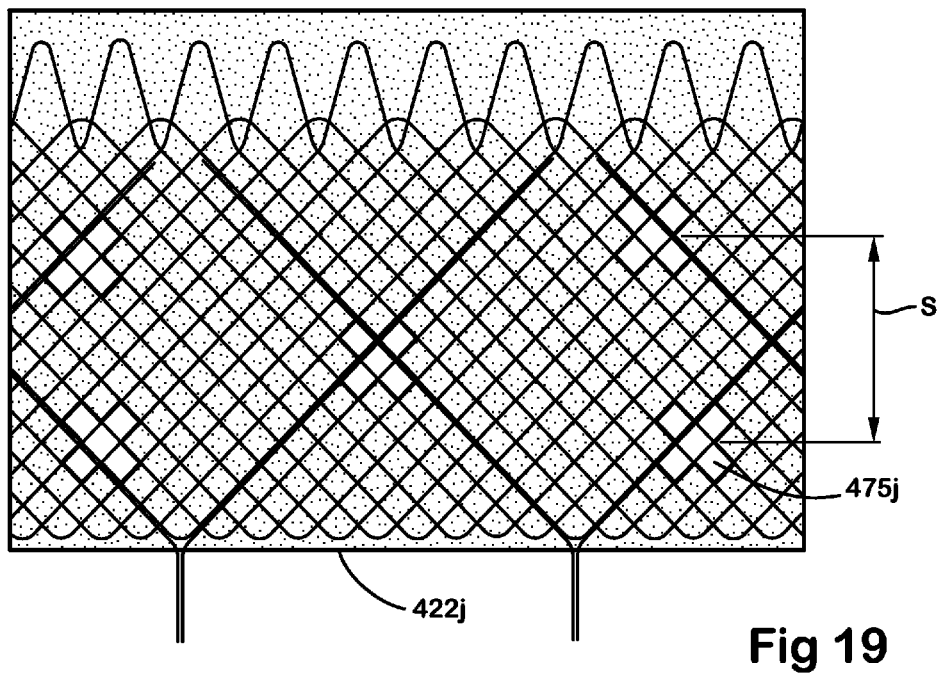
FIG. 19 is the same view as FIG. 10 of an alternative embodiment thereof.

FIGS. 17, 18 and 19 show bariatric devices having respective flattened esophageal members 422h, 422i and 422j, each having respective openings 475h, 475i, and 475j in the shape of a cross defined by intersecting lines of three (3) open cells each. However, the openings are arranged differently in each esophageal member. Other opening shapes and arrangements will be apparent to the skilled arisen.

Figure 20:
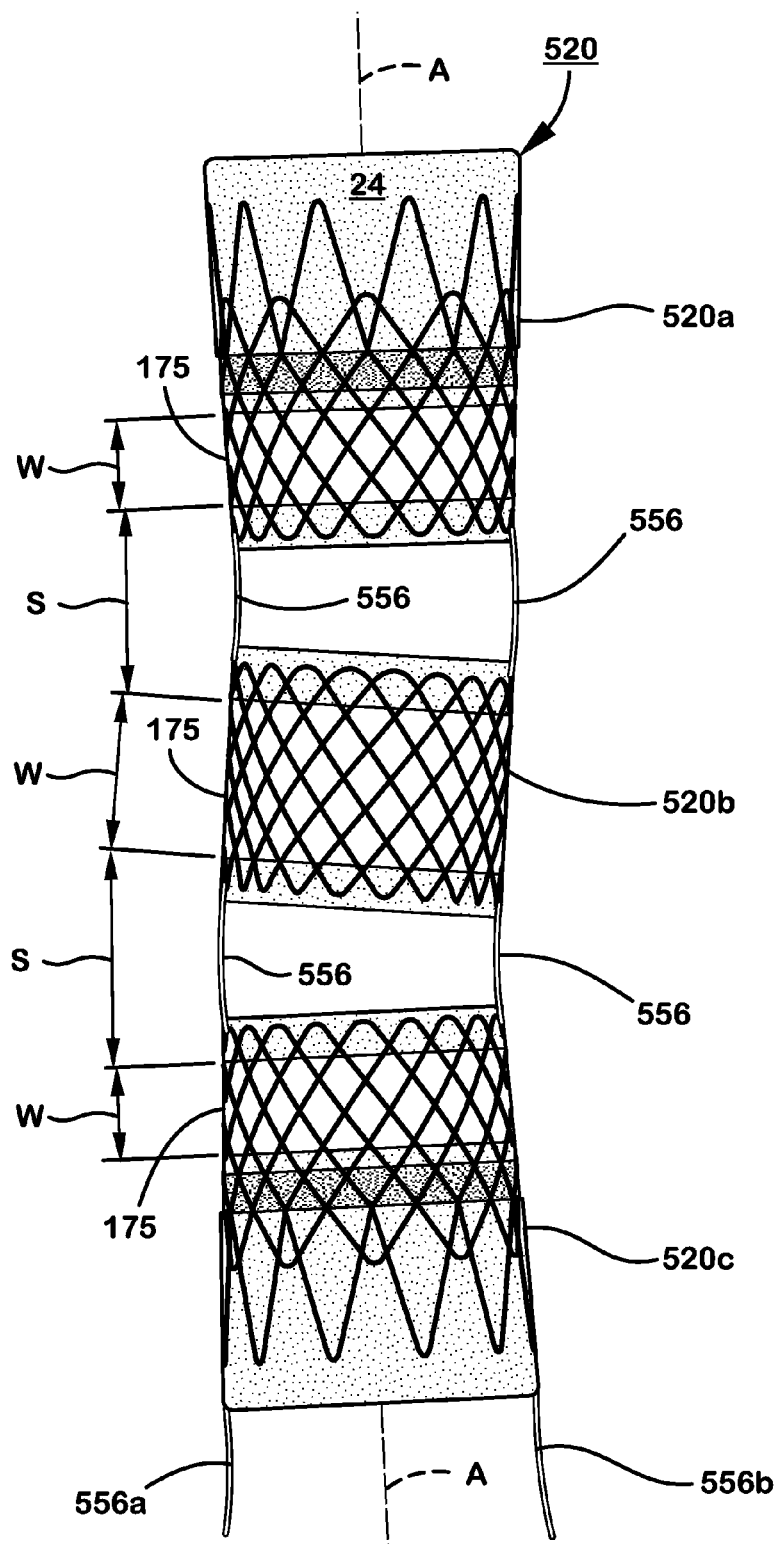
FIG. 20 is the same view as FIG. 1 of an alternative embodiment thereof.
Figure 21:
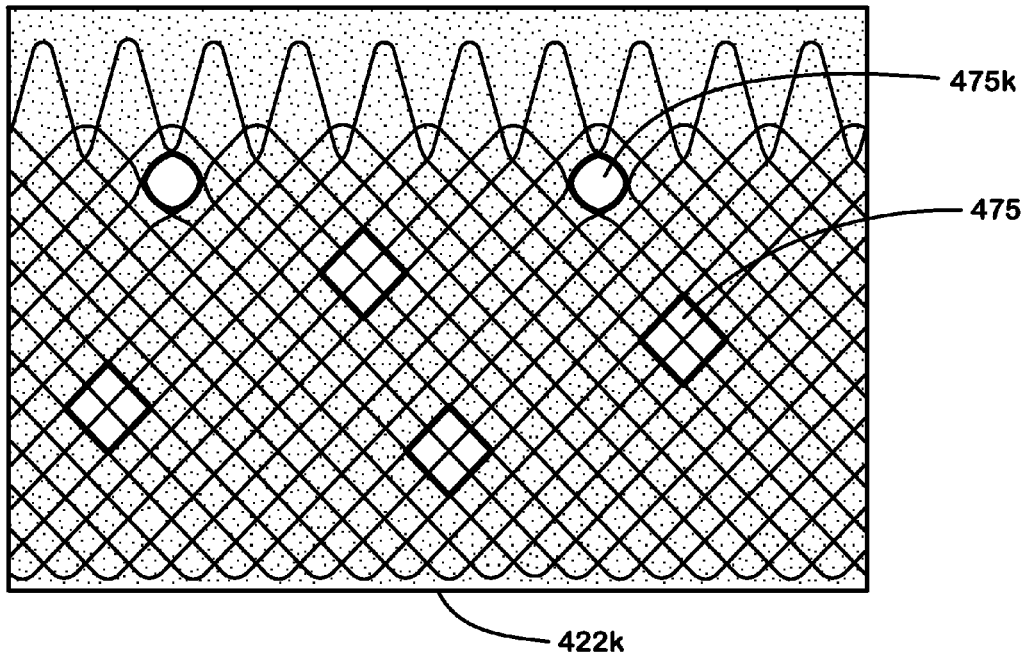
FIG. 21 is the same view as FIG. 10 of an alternative embodiment thereof.
Figure 22:
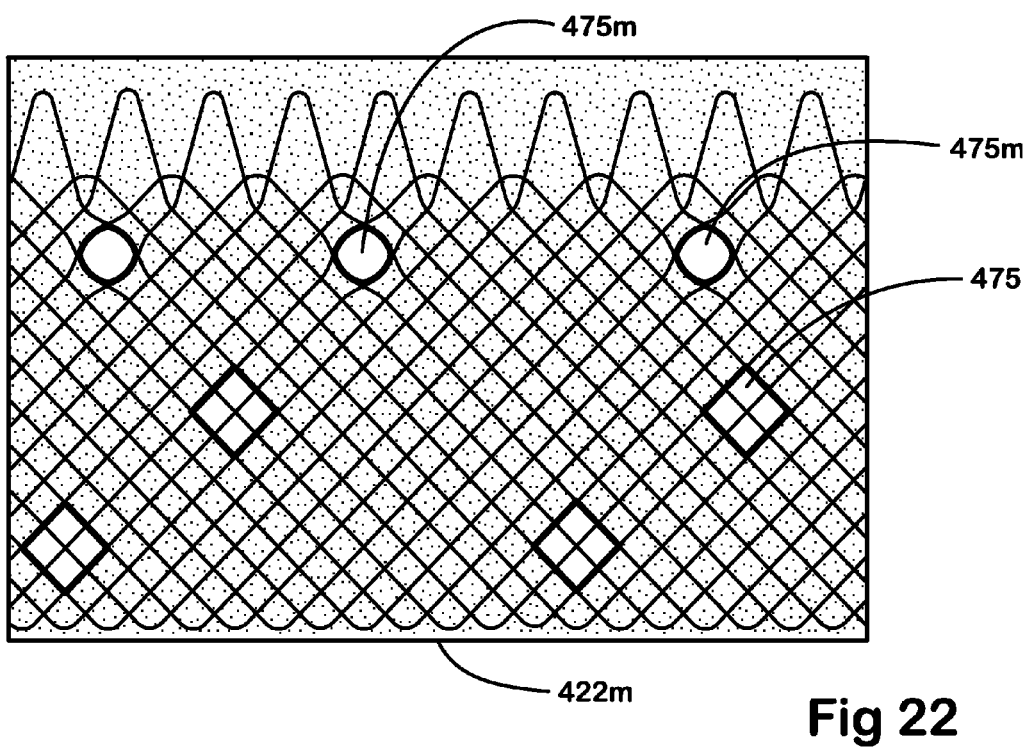
FIG. 22 is the same view as FIG. 10 of an alternative embodiment thereof.
Figure 23:
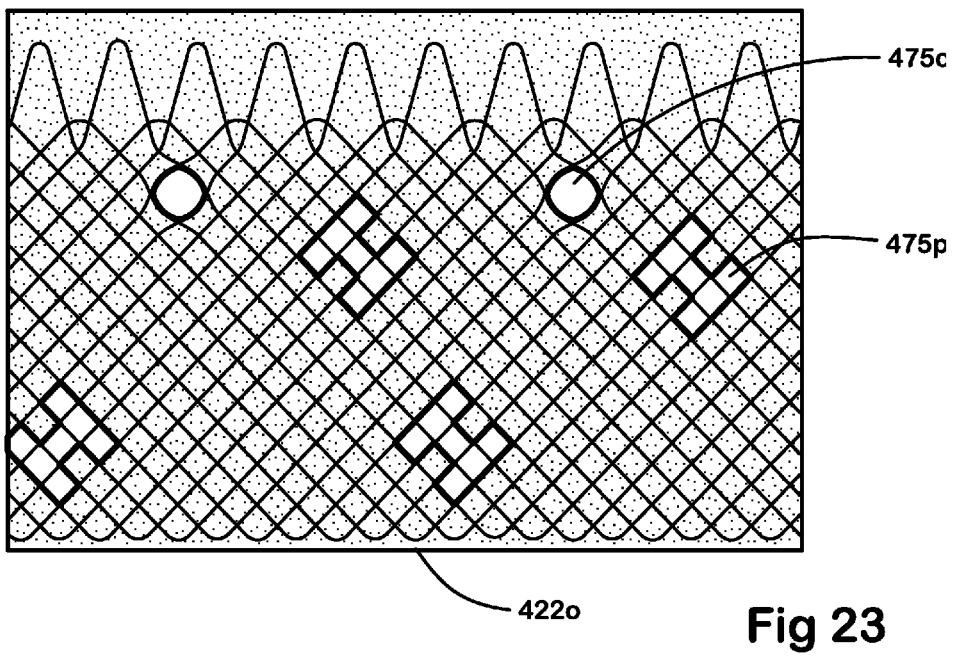
FIG. 23 is the same view as FIG. 10 of an alternative embodiment thereof.
Figure 24:
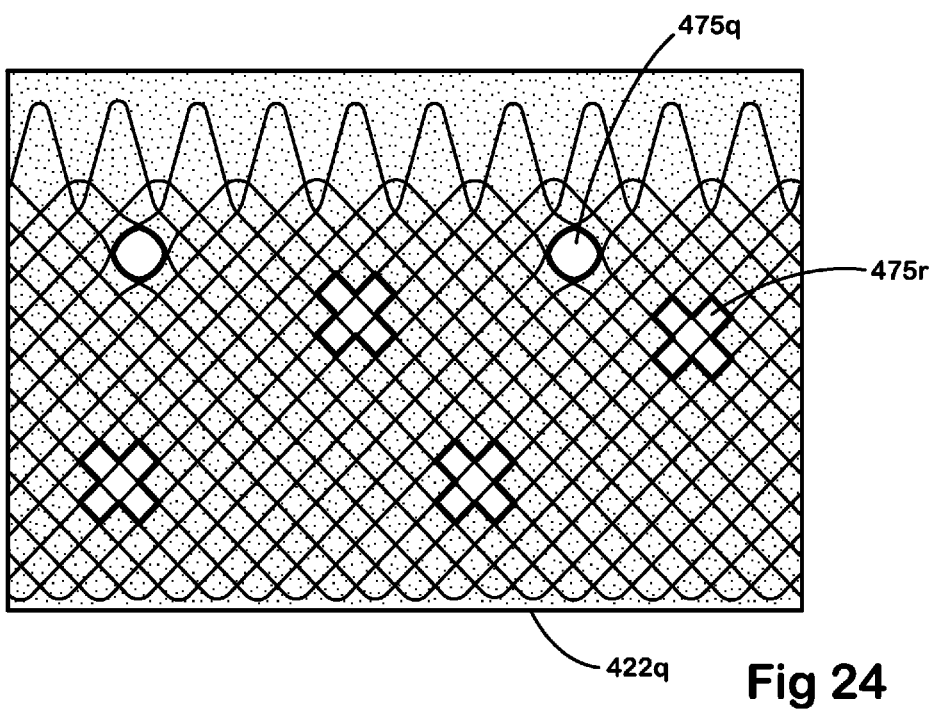
FIG. 24 is the same view as FIG. 10 of an alternative embodiment thereof.
Figure 25:
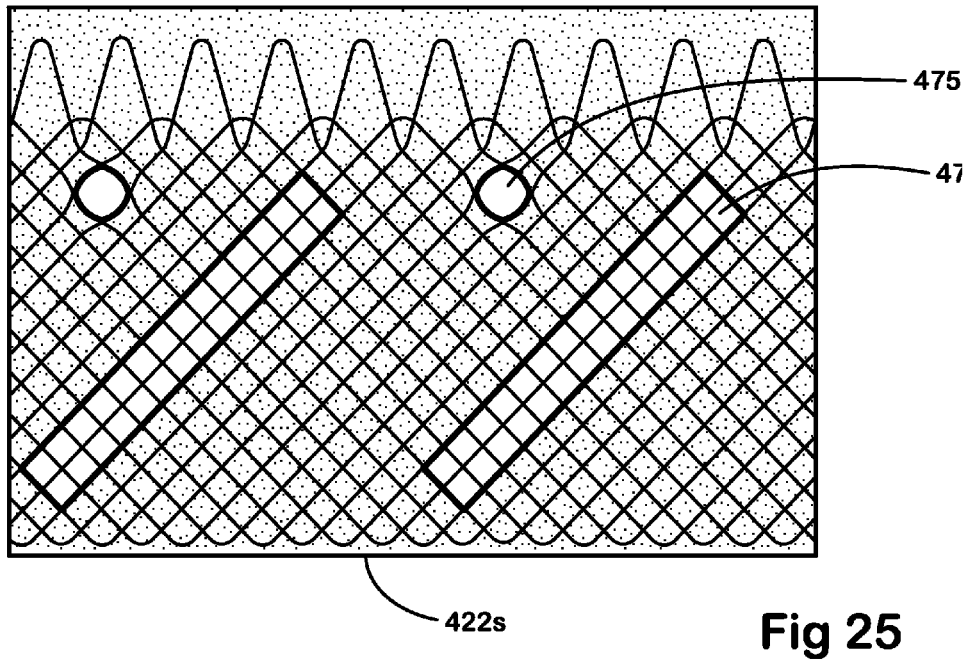
FIG. 25 is the same view as FIG. 10 of an alternative embodiment thereof.
Figure 26:
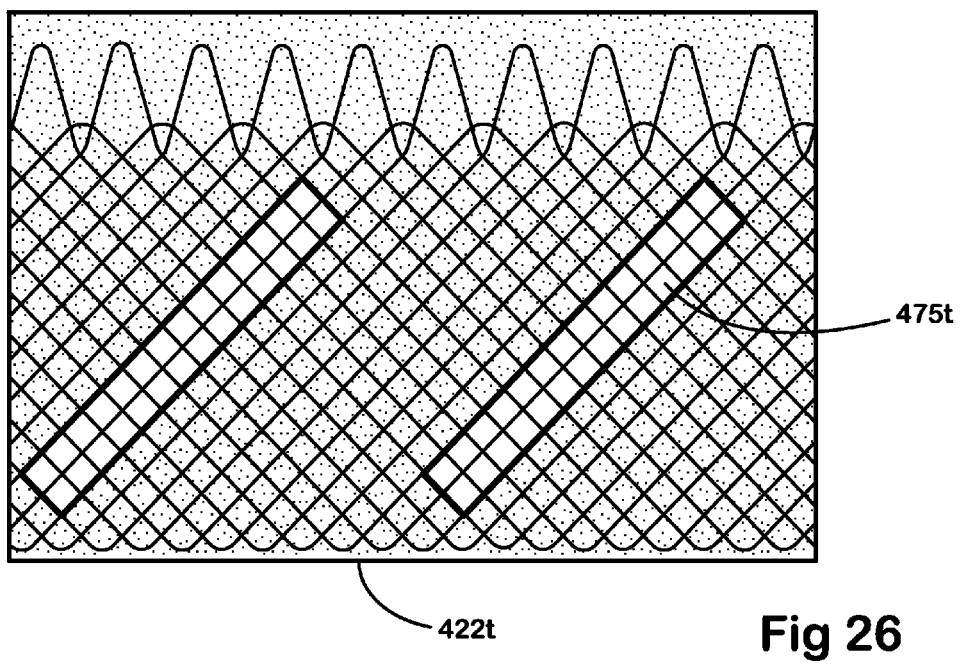
FIG. 26 is the same view as FIG. 10 of an alternative embodiment thereof.

The esophageal member 520, shown in FIG. 20, is made up of sections 520a, 520b, 520c that are joined together with flexible struts 456. Each section 520a, 520b, 520c has an opening 175 so that openings 175 are spaced apart a distance S that is at least an order of magnitude of an esophageal peristaltic wavelength. In this manner, at least one opening 175 will be firmly engaged by the esophagus as the peristaltic wave passes. While illustrated as connected by separated struts 556, the sections could be joined by a common cover, but just be made up of separate mesh sections, which could themselves be made up of Nitinol wire mesh, stainless steel or polymers. Also, esophageal member 520 is shown with two struts 556a, 556b that connect member 520 with a cardiac member (not shown in FIG. 20). However, it should be understood that each section 520a, 520b and 520c may individually be connected by struts to the cardiac member so that there is always tension applied to the cardiac member as the esophageal peristaltic wave passes.

FIGS. 21-26 show a variety of flattened esophageal members 422K, 422M, 422O, 422Q, 422S and 422T, each with some form of opening 475L, 476N, 475P, 475R, and 475T that provide openings which expose at least a portion of the mesh on one cover surface for mucosal capture and ingrowth about the wires of the mesh. At least some of the flattened esophageal members have openings 475K, 475M, 475O, 475Q and 475S, which do not get traversed by a mesh section and are intended primarily for mucosa capture. The openings 475K, 475M, 475O, 475O and 475S are large enough that a larger portion of the mucosa may be captured therein for temporary fixation until tissue ingrowth occurs in all of the openings and may be aided by suction, injection by a collagen filler to make the mucosa larger in diameter, or the like.

While the foregoing description describes several embodiments of the present invention, it will be understood by those skilled in the art that variations and modifications to these embodiments may be made without departing from the spirit and scope of the invention, as defined in the claims below. The present invention encompasses all combinations of various embodiments or aspects of the invention described herein. It is understood that any and all embodiments of the present invention may be taken in conjunction with any other embodiment to describe additional embodiments of the present invention. Furthermore, any elements of an embodiment may be combined with any and all other elements of any of the embodiments to describe additional embodiments.

The embodiments of the invention in which an exclusive property or privilege is claimed are defined as follows:

1. An intraluminal device, comprising:
   a surface defined by a wall having opposite end portions, said surface being configured to generally conform to the shape and size of a portion of the lumen with said end portions spaced apart along an axis in the direction of peristaltic movement along the lumen;
   said wall being self-expanding outwardly and having at least two openings therein between said end portions wherein tissue enters the at least two openings in order to resist peristaltic waves causing distal migration of the device, wherein said wall is defined by a support structure and a cover over said support structure, said at least two openings defined in said cover, wherein said at least two openings are spaced apart along said axis a distance that is at least on the order of magnitude of a wavelength of a peristaltic wave in the lumen so that there will be an area of increasing pressure of the lumen acting on at least one of said openings which is thereby engaging the lumen to anchor the wall even with an area of decreasing pressure acting on the other of the at least two openings as the peristaltic wave passes the device.

2. The intraluminal device as claimed in claim 1 wherein said wall is generally cylindrical with respect to the axis and wherein each of said at least two openings comprise a plurality of openings that are distributed radially around a circumference of said wall.

3. The intraluminal device as claimed in claim 2 wherein each of said plurality of openings are distributed radially around a circumference of said wall in a pattern.

4. The intraluminal device as claimed in claim 3 wherein said patterns are arranged generally perpendicular to the axis.

5. The intraluminal device as claimed in claim 4 wherein said patterns are spaced apart a distance that is at least on the order of magnitude of a wavelength of a peristaltic wave of the lumen.

6. The intraluminal device as claimed in claim 2 wherein each said plurality of openings comprises a discrete opening.

7. The intraluminal device as claimed in claim 5 wherein said patterns are spaced apart a distance that is at least approximately the wavelength of the peristaltic wave of the lumen.

8. The intraluminal device as claimed in claim 1 wherein each of said at least two openings comprises an open band extending substantially around said wall generally perpendicular to the axis.

9. The intraluminal device as claimed in claim 1 wherein said support structure is defined by a plurality of intersecting mesh portions thereby defining a plurality of rectilinear polygons and wherein said at least two openings being discrete openings each the size of a plurality of adjacent ones of said polygons and separated from each other by said cover.

10. The intraluminal device as claimed in claim 9 wherein each said at least two openings is the size of at least three of said adjacent ones of said polygons arranged in shapes comprising at least one selected from a diamond, a cross, a line and an "H" shape.

11. The intraluminal device as claimed in claim 1 wherein each of said at least two openings is configured to regulate mucosal ingrowth on the support structure.

12. The intraluminal device as claimed in claim 11 wherein each of said at least two openings is configured to regulate mucosal ingrowth by having a dimension that is less than an amount that would promote uncontrolled mucosal ingrowth.

13. The intraluminal device as claimed in claim 11 wherein each of said at least two openings is configured to regulate mucosal ingrowth by said cover extending on a side of said support structure at said at least one opening that is opposite a side that is adapted to contact the mucosa.

14. The intraluminal device as claimed in claim 1; wherein said support structure comprises an outwardly extending mesh.

15. The intraluminal device as claimed in claim 1 wherein said surface is configured to generally conform to the shape and size of a portion of one chosen from i) the esophagus, ii) the intestine, iii) the fallopian tube, iv) the ureter, v) the urethra, vi) the vas deferens, and vii) the biliary duct.

16. An intraluminal device, comprising:
an esophageal member having an esophageal surface defined by an esophageal wall, said esophageal surface being configured to generally conform to the shape and size of a portion of the esophagus, a cardiac member having a cardiac wall defining a cardiac surface that is configured to generally conform to the shape and size of a portion of the cardiac region of the stomach and a connector connected with said esophageal member and said cardiac member, at least one chosen from i) said esophageal member and ii) said cardiac member is adapted to stimulate receptors in order to influence a neurohormonal mechanism in the recipient to cause at least partial satiety by augmenting fullness caused by food and simulating fullness in the absence of food;
wherein said esophageal wall being self-expanding outwardly and having end portions spaced apart along an axis in the direction of peristaltic movement along the esophagus and having at least two openings therein between said end portions, wherein said esophageal wall is defined by a support structure and a cover over said support structure, said at least two openings defined in said cover, wherein mucosa enters the at least two openings in order to resist peristaltic waves causing distal migration of said esophageal member wherein said at least two openings are spaced apart along said axis a distance that is at least on the order of magnitude of a wavelength of a peristaltic wave of the esophagus so that there will be an area of increasing pressure of the lumen acting on at least one of said openings which is thereby engaging the lumen to anchor the wall even with an area of decreasing pressure acting on the other of the at least two openings as the peristaltic wave passes the esophageal wall.

17. The intraluminal device as claimed in claim 16 wherein said esophageal wall is generally cylindrical with respect to the axis and wherein each of said at least two openings comprise a plurality of openings that are distributed radially around a circumference of said esophageal wall.

18. The intraluminal device as claimed in claim 17 wherein said plurality of openings are distributed radially around a circumference of said esophageal wall in a pattern.

19. The intraluminal device as claimed in claim 18 wherein each of said patterns are arranged generally perpendicular to the axis.

20. The intraluminal device as claimed in claim 19 wherein said patterns are spaced apart a distance that is on the order of magnitude of a wavelength of a peristaltic wave of the esophagus.

21. The intraluminal device as claimed in claim 20 wherein said patterns are spaced apart a distance that is at least approximately the wavelength of the peristaltic wave of the esophagus.

22. The intraluminal device as claimed in claim 17 wherein each said plurality of openings comprises a plurality of discrete openings extending substantially around said esophageal wall.

23. The intraluminal device as claimed in claim 16 wherein each of said at least two openings comprises an open band extending substantially around said esophageal wall generally perpendicular to the axis.

24. The intraluminal device as claimed in claim 16 wherein said support structure is defined by a plurality of intersecting mesh portions thereby defining a plurality of rectilinear polygons and wherein said openings being discrete openings each the size of a plurality of adjacent ones of said polygons and separated from each other by said cover.

25. The intraluminal device as claimed in claim 24 wherein each said at least two openings being the size of at least three of said adjacent ones of said polygons arranged in shapes comprising at least one selected from a diamond, a cross, a line and an "H" shape.

26. The intraluminal al device as claimed in claim 16 wherein each of said at least two openings is configured to regulate mucosal ingrowth on the support structure.

27. The intraluminal device as claimed in claim 26 wherein each of said at least two openings is configured to regulate mucosal ingrowth by having a dimension that is less than an amount that would promote uncontrolled mucosal ingrowth.

28. The intraluminal device as claimed in claim 26 wherein each of said at least two openings is configured to regulate mucosal ingrowth by said cover extending on a side of said support structure at said at least one opening that is opposite a side that is adapted to contact the mucosa.

29. The intraluminal device as claimed in claim 24 wherein said support structure comprises an outwardly extending mesh.

30. The intraluminal device as claimed in claim 16 further including at least one opening is of a size to allow mucosa to be captured therein by suction.

31. The intraluminal device as claimed in claim 30 including a band placed over the captured mucosa.

32. A method of fixing an intraluminal device in a lumen subject to peristalsis, comprising:

positioning an intraluminal device in a lumen that is subject to peristaltic waves, said intraluminal device including a surface defined by a wall having opposite end portions, said surface being configured to generally conform to the shape and size of a portion of the lumen with said end portions spaced apart along an axis in the direction of peristaltic movement along the lumen; and wherein said wall having at least two openings therein between said end portions, wherein said esophageal wall is defined by a support structure and a cover over said a support structure, said at least two openings defined in said cover, wherein said wall being self-expanding outwardly to contact the lumen to cause tissue to enter the at least two openings in order to resist peristaltic waves causing distal migration of the device wherein said at least two openings are spaced apart along said axis a distance that is at least on the order of magnitude of a wavelength of a peristaltic wave in the lumen so that there will be an area of increasing pressure of the lumen acting on at least one of said openings which is thereby engaging the lumen as the peristaltic wave passes the device.

33. A method of fixing an intraluminal device in a recipient, said method comprising:

positioning an intraluminal device in a recipient, said intraluminal device having an esophageal member with an esophageal surface defined by an esophageal wall, said esophageal surface being configured to generally conform to the shape and size of a portion of the esophagus, a cardiac member having a cardiac wall defining a cardiac surface that is configured to generally conform to the shape and size of a portion of the cardiac region of the stomach and a connector connected with said esophageal member and said cardiac member, wherein said esophageal wall having end portions spaced apart along an axis in the direction of peristaltic movement along the esophagus and having at least two openings therein between said end portions, wherein said esophageal wall is defined by a support structure and a cover over said support structure, said at least two openings defined in said cover;

wherein said esophageal wall being self-expanding outwardly to contact the esophagus to cause esophageal tissue to enter the at least two openings to resist distal migration of the esophageal member, wherein said at least two openings are spaced apart along said axis a distance that is at least on the order of magnitude of a wavelength of a peristaltic wave of the esophagus so that there will be an area of increasing pressure of the esophagus on at least one of said at least two openings which is thereby engaging the esophagus to anchor the esophagus wall even with an area of decreasing pressure acting on the other of the at least two openings as the peristaltic wave passes the esophageal wall.

* * * * *